US 6,672,129 B1

(12) United States Patent  
Frederickson et al.

(10) Patent No.: US 6,672,129 B1
(45) Date of Patent: *Jan. 6, 2004

(54) METHOD FOR CALIBRATING A SENSOR FOR MEASURING CONCENTRATION OF ODORS

(75) Inventors: Christopher J. Frederickson, Little Elm, TX (US); Donald J. Hayes, Plano, TX (US); David B. Wallace, Dallas, TX (US); David W. Taylor, Dallas, TX (US); Matthew D. Hayes, Plano, TX (US)

(73) Assignee: MicroFab Technologies, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/067,224

(22) Filed: Feb. 7, 2002

Related U.S. Application Data

(62) Division of application No. 09/845,714, filed on Apr. 30, 2001, now Pat. No. 6,390,453, which is a continuation of application No. 09/176,818, filed on Oct. 22, 1998, now abandoned.
(60) Provisional application No. 60/062,727, filed on Oct. 22, 1997.

(51) Int. Cl.[7] .......................... G01N 37/00; G01N 33/48
(52) U.S. Cl. .......................... 73/1.06; 73/23.34; 347/20
(58) Field of Search .................. 73/1.01–1.06, 73/23.34, 23.3, 81.03, 863.02, 863.03, 863.11, 965.7

(56) References Cited

U.S. PATENT DOCUMENTS

| 4,159,672 A | 7/1979 | Gargnilo et al. ............ 454/337 |
| 4,265,248 A | 5/1981 | Chuiton et al. ............. 600/303 |
| 4,310,474 A | 1/1982 | Iyengar ........................ 261/1 |
| 4,812,856 A | 3/1989 | Wallace ........................ 347/89 |
| 4,895,017 A | * 1/1990 | Pyke et al. ................. 73/24.06 |
| 4,911,892 A | 3/1990 | Grace et al. .................. 422/94 |
| 5,053,100 A | 10/1991 | Hayes et al. ................ 156/294 |
| 5,145,645 A | 9/1992 | Zzkin et al. .................. 422/98 |
| 5,177,994 A | 1/1993 | Moriizumi et al. ......... 73/23.29 |
| 5,208,980 A | 5/1993 | Hayes ........................ 29/890.1 |

(List continued on next page.)

FOREIGN PATENT DOCUMENTS

| AU | AUB70632/94 | 6/1994 |
| EP | 0432992 A1 | 6/1991 |
| EP | 0542723 A2 | 5/1993 |
| GB | 2272389 | 5/1994 |
| WO | WO 92/11050 | 7/1992 |
| WO | WO 93/10910 | 6/1993 |

OTHER PUBLICATIONS

Marsili, R., "The Electronic Nose", Jun. 1995, Food Product Design, available from the Internet at http://www.foodproductdesign.com/archive/1995/0695QA.html.*

(List continued on next page.)

Primary Examiner—Hezron Williams
Assistant Examiner—David Rogers
(74) Attorney, Agent, or Firm—Locke Liddell & Sapp LLP

(57) ABSTRACT

A method and apparatus is disclosed which employs a pulse-controlled microdroplet fluid delivery system for precisely dispensing fragrances and other odor producing vapors. The pulse-controlled fluid delivery device is capable of ejecting microdroplets of fluid with a diameter less than 350 micrometers at a controlled ejection rate based upon inkjet printing technology. The pulse-controlled fluid delivery system includes mechanisms for vaporizing the fluids and delivery of the vapors to the nose, which is controlled by a programmable system controller capable of real time data-driven dispensing with a multi-fluid capability. Synthesis of custom fragrances is made possible by a multijet programmed control system which adjusts dispensing rates of components. Calibration of a prior art "electronic nose" is disclosed. A precise calibration gas is produced in real-time to counteract the effect of drifting.

8 Claims, 15 Drawing Sheets

U.S. PATENT DOCUMENTS

| | | | |
|---|---|---|---|
| 5,227,813 A | 7/1993 | Pies et al. | 347/71 |
| 5,229,016 A | 7/1993 | Hayes et al. | 222/590 |
| 5,284,133 A | 2/1994 | Burns et al. | 128/200.23 |
| 5,402,162 A | 3/1995 | Fusting et al. | 347/43 |
| 5,435,060 A | 7/1995 | Hayes et al. | 29/890.1 |
| 5,461,403 A | 10/1995 | Wallace et al. | 347/10 |
| 5,508,200 A | 4/1996 | Tiffany et al. | 436/44 |
| 5,511,726 A | 4/1996 | Greenspan et al. | 239/102.2 |
| 5,565,148 A | 10/1996 | Pendergrass, Jr. | 261/30 |
| 5,591,409 A | 1/1997 | Watkins | 422/110 |
| 5,658,802 A | 8/1997 | Hayes et al. | 436/518 |
| 5,666,145 A | 9/1997 | Hayes et al. | 347/71 |
| 5,681,757 A | 10/1997 | Hayes | 257/778 |
| 5,756,879 A | 5/1998 | Yamagishi et al. | 73/28.01 |
| 5,777,207 A | 7/1998 | Yun et al. | 73/31.05 |
| 5,801,297 A | 9/1998 | Mifsud et al. | 73/23.34 |
| 5,849,208 A | 12/1998 | Hayes et al. | 216/94 |
| 5,894,841 A * | 4/1999 | Voges | 128/203.12 |
| 5,904,916 A | 5/1999 | Hirsch | 424/45 |
| 6,325,475 B1 | 12/2001 | Hayes et al. | 347/2 |
| 6,339,897 B1 | 1/2002 | Hayes et al. | 43/132.1 |

OTHER PUBLICATIONS

Baltes, Lange & Koll, "'The electronic nose in Lilliput',' IEEE Spectrum, p. 35–38, (Sep. 3, 1998).

Kaplan & Braham, "The How and Why of Elctronic Noses", IEEE Spectrum, p. 22–34, (Sep. 3, 1998).

Cain, Cometto–Muniz, WIJK, "Techniques in the Quantitative Study of Human Olfaction", In Science of Olfaction, Chapter. 9, p. 279–308, ( Aug. 6, 1992).

* cited by examiner

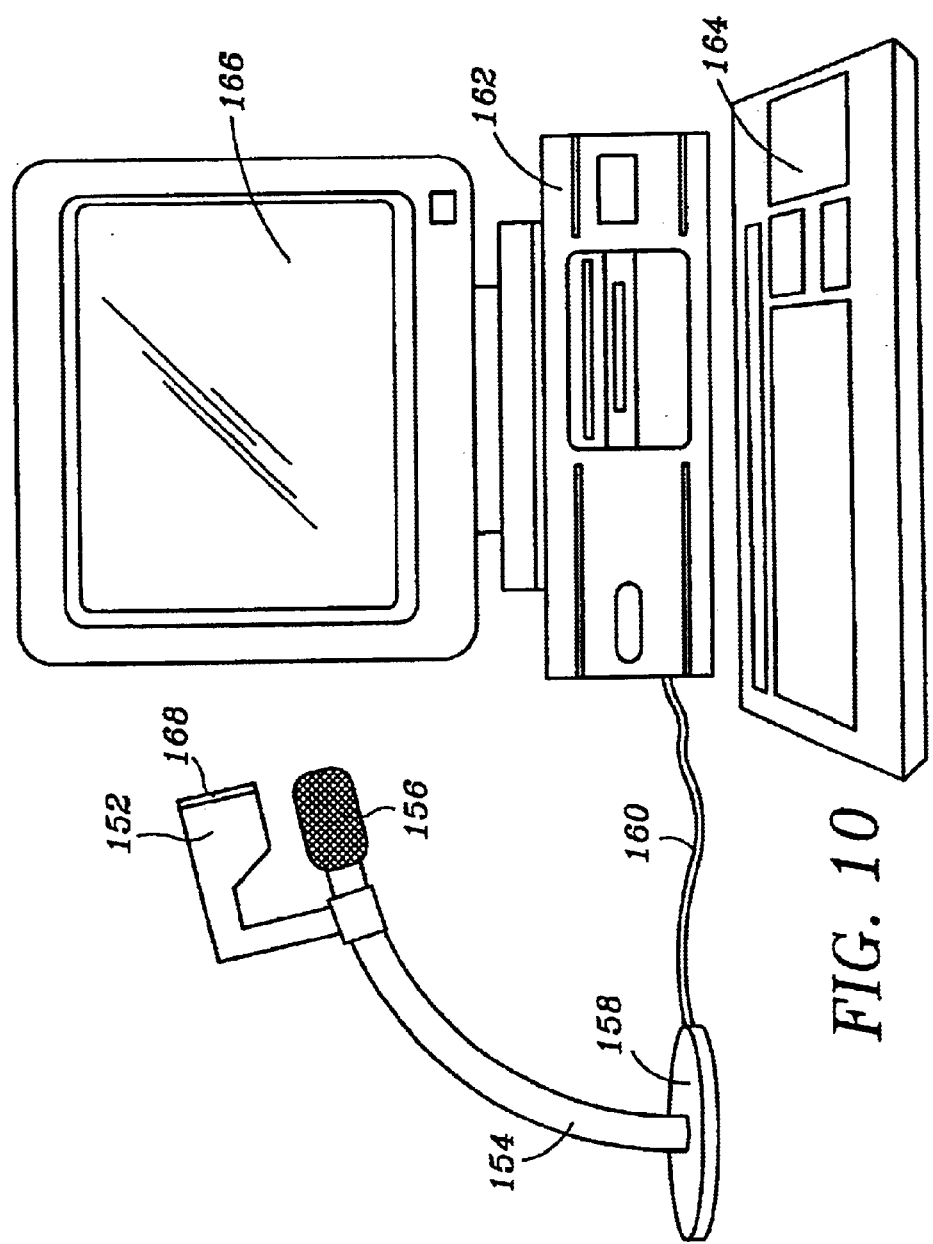
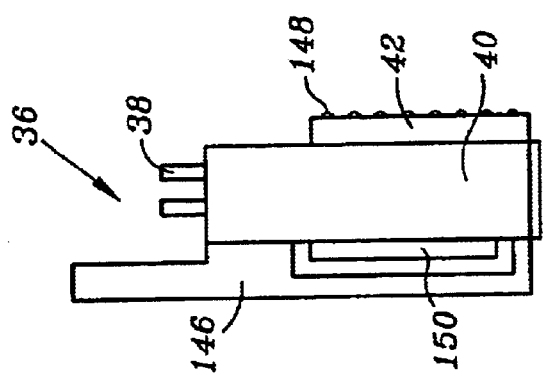
FIG. 10
FIG. 9

| Ingredients | Setting | Rate | % |
|---|---|---|---|
| Rose | | 250 | 27 |
| Anise | | 100 | 11 |
| Orange Blossom | | 10 | 1 |
| Tangerine | | 25 | 3 |
| Ginger | | 40 | 4 |
| Orchid | | 50 | 5 |
| Iris | | 120 | 13 |
| Yang-Yang | | 100 | 11 |
| Vanilla | | 80 | 8 |
| Amber | | 50 | 5 |
| Musk | | 100 | 11 |

FIG. 11

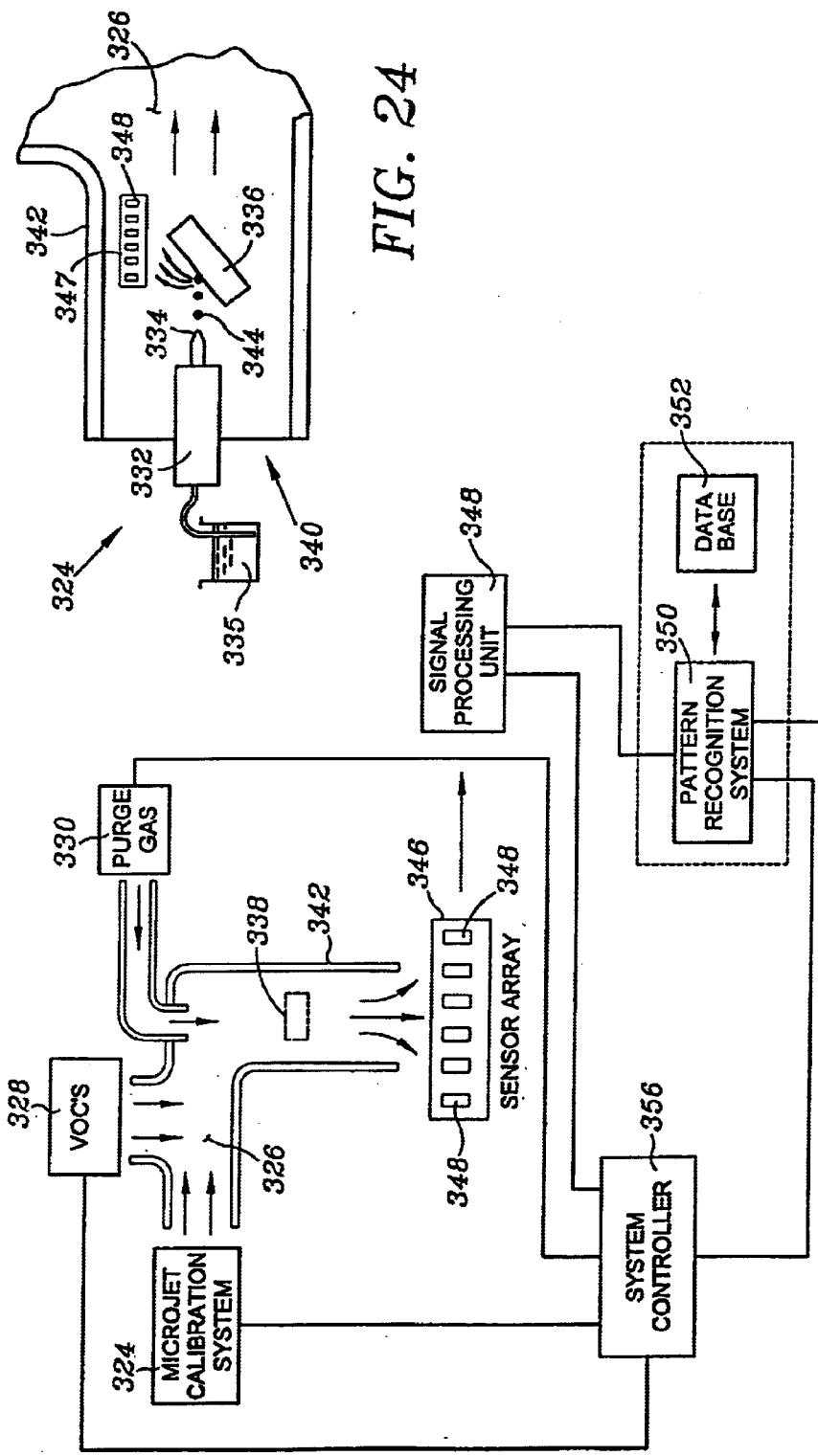

METHOD FOR CALIBRATING A SENSOR FOR MEASURING CONCENTRATION OF ODORS

CROSS REFERENCE TO RELATED APPLICATIONS

This application is a divisional of U.S. patent application Ser. No. 09/845,714, entitled "Method and Apparatus for Delivery of Fragrances and Vapors to the Nose", filed on Apr. 30, 2001 and now U.S. Pat. No. 6,390,453, which is a continuation of U.S. patent application Ser. No. 09/176,818 filed Oct. 22, 1998 and now abandoned entitled "Method and Apparatus for Delivery of Fragrances and Vapors to the Nose", which in turn was a continuation-in-part of prior application Ser. No. 60/062,727 filed Oct. 22, 1997 and now abandoned, the benefit of which is claimed in this application under 35 U.S.C. § or §119(e), as the case may be.

This invention was made with government support under a grant or contract awarded by the National Institute of Mental Health. The United States government may have certain rights in this invention.

FIELD OF THE INVENTION

The present invention relates to methods and apparatus for precisely dispensing fragrances and other volatile materials, synthesizing custom fragrances in real time and calibration of electronic sensors.

BACKGROUND OF THE ART

Odoriferous substances can be dispensed by numerous methods including passive wicks, aerosol "puffers", fine particle sprayers and scented candles. Control of the initiation and cessation of sensory experience resulting from conventional dispensing is very difficult. Except in a gross sense, the quantity of odor producing material dispensed is not controlled. It is particularly difficult to cease producing an aroma sensation once begun and miniaturization is not readily achieved. Passive dispensing devices such as wicks or candles require material that remain relatively stable in air as a vapor and are able to withstand heat, for example. Materials which are readily oxidized at room temperature, photodecompose or hydrolyze in humid air are all examples of evanescent fragrances for which periodic active dispensing is the only practical way to produce the fragrance.

The most common method of dispensing fragrances or aromas is the wick method in which a wick in contact with a volatile liquid is exposed in a space. It is evident that once the wick is exposed, there is no way to control the amount of material dispensed nor to easily adjust it or quantify it. It can't conveniently be turned on and off. None of the conventional devices for distributing odor producing chemicals are subject to digital control or quantitative precision dispensing.

The prior art uses the same dispensing methods for the purpose of odor masking or eliminating vapors. Three approaches to removal of bad orders can be considered: A) perceptual masking, B) specific or nonspecific olfactory receptor blockade and C) odor molecule binding or metabolism. It would be desirable to have a precise active jet dispensing method for all three of these approaches because it allows the best odor removal materials to be dispensed interactively, in response to the presence of any specific bad odor. All of these strategies are in part used by companies such as EnviroCon, AMAX, Elim-N-Odor, Inc., BioZapp Labs, inc., Technaal, Inc.; and OdorGone (Ray Market).

Perceptual masking is an approach whereby a competing smell is introduced in a sufficient intensity to "mask" the offending odor whereby the subject is aware of both odors but with reduced attention paid to the offending odor. Olfactory receptor blockade can be an effective odor removal strategy if the offensive order is detected by a single receptor type in the nose whereby pharmacologic blockade of that specific receptor with a receptor blocking ligand, will produce a specific "smell blindness" for that smell. This is superior to the use of vapors of formaldehyde or cocaine or zinc oxide cream which have been used as non-specific receptor blocking agents which cause complete anosmia or hyposmia. Odor molecule removal by catabolysis of the molecule or binding another macromolecule to it can both remove the materials from the air and thus remove the odor. There are commercially available products intended to remove specific odors by one of these methods. All of these approaches could benefit from a device or method that would provide dispensing accuracy and precise control.

There is a significant need for accurate controlled dispensing of pharmaceuticals, herbs and psychoactive substances of all types. Potent psycho-active materials like cocaine, adrenalin, and amphetamine can be electronically dispensed from physician's direction using devices such as inhalers. Specific chemicals to control asthma are examples of such use. A more precise method of dispensing would be expected to produce an improvement in controlled dosage. Emergency personnel and military are obviously targets for emergency psycho-stimulant use. Nonprescription drugs like caffeine, nicotine, theopholine, ginseng, and others could also be dispensed in inhalable formulations for use in a variety of medical or even non-medical applications. Pheromones or other natural or synthetic materials that alter behavior and physiology via a nasal inhalation route are also subjects for precise controlled dispensing. Odoriferous materials that affect mood, arousal, stress or other dimensions of human behavior and physiology through primarily olfactory perceptual routes can benefit from improved dispensing apparatus. The invention of this application is a superior method for dispensing such compounds because dispensing can be precise, metered, interactive, and the dispenser can be tamperproof with prescribed dispensing rates possible. It would be desirable to have a dispensing device that was both discreet, digital and programmable, and in many foreseeable applications desirable to provide miniature devices which take up less space and are economical to manufacture and produce. The present invention makes these possible.

SUMMARY OF THE INVENTION

The present invention is directed to ink-jet based systems for the micro-dispensation and vaporization of volatile materials obtained from odor producing fluids or materials which can be melted or dissolved in fluids. The invention relies upon tiny electronically operated fluid droplet ejection devices having a fluid supply reservoir and a droplet ejection orifice aimed to deposit fluid droplets onto a target medium or space. The fluid supply reservoir is provided with a viscosity adjusted odor sensation producing fluid which is ejected in a stream of sequential droplets in response to electrical signals comprising voltage pulses. The preferred fluid droplet ejection device comprises one or more piezoelectric actuators but ejection devices can be made with other types of actuators such as magnetoresistive, inductive, thermal or miniature pressure solenoid valve. Pulses are provided by drive electronics operably connected to the ejection device or a plurality of such ejection devices and a system controller operably connected to the drive electronics and a power source whereby operating signals are delivered to the drive electronics to cause sequential droplets of fluid to be deposited onto the target medium or space. A typical orifice size is approximately 60 micrometers. Droplets in the range of 10 micrometers to over 350 micrometers are possible by varying known parameters of ink-jet printing heads.

In one embodiment the fluid droplet ejection device or devices are enclosed in a housing containing a target medium and air-flow outlet. In a variation of the invention, the target medium is a heater having a heated surface operated by the system controller and positioned to intercept ejected droplets deposited thereon. Air moved by an air movement device may be used to increase volatilization of fluid deposited on the target medium by the ejection device. The heater has little or no heat sink characteristics because of its low mass and small size. The heater has a quickly heatable surface upon which fluid droplets are deposited which equally quickly falls back to ambient temperature when not powered.

In a further variation, the heater is a plurality of heaters individually controlled to quickly raise the temperature of the heatable surfaces to vaporized fluid droplets deposited thereon when the ejection device is operated and return to an unheated state when ejection ceases in order to control vaporization of deposited fluid. In some applications the heater temperature is preset, based upon the fluid being ejected, and held constant at the specified temperature. Air movement means may be used to force air over the heated surface or surfaces and thereby carry vapor from a passageway through the air-flow outlet. Individual fluid droplet ejection devices including the reservoir have been produced having a length less than one centimeter and a diameter less than two millimeters. Such miniaturization makes new applications and methods possible in connection with dispensing fragrance, aroma and odor producing materials.

The present invention has utility in applications such as a virtually reality display system for entertainment or training, instrumentation including medical instrumentation, conditioning of environments, odor masking systems, fragrance synthesis, medication delivery, computer output systems (fragrance display), communication systems and calibration inputs for electronic chemical sensor systems.

In another embodiment of the invention, a printhead having a plurality of electronically operated fluid droplet ejection channels each having a fluid supply reservoir containing volatile fluids which produce different aromas or fragrance components. The channels are selectively operated by a system controller to deposit fluid on a target medium where they can volatilize to produce a custom aroma or fragrance In combination with a programmed computer which selectively operates the fluid droplet ejection channels in different combinations or at different rates or upon differentially heated surfaces, a unique and reproducible fragrance or aroma can be produced and reproduced. By altering the selection of fragrance components or the relative amounts thereof, an original odor effect can be quickly and precisely changed to produce a second or a third or more different odor effect merely by changing the voltage pulse signals which operate selected channels.

The microdispensing ink-jet based systems of the present invention allow the study of numerous properties of the sense of smell, including studies of temporal integration times, inter-nostril summation, backwards and forwards masking, and other phenomena that have only received cursory attention due to methodological limitations based on existing systems. The microdispensing ink-jet based systems of the present invention provide precise control of both the temporal envelope of the stimulus and the total number of molecules constituting the stimulus. Although conventional olfactory testing machines are available, only large well-funded organizations can afford them because of high costs.

The present invention provides a means for conducting such research at a fraction of the cost of conventional olfactory research testing equipment. In addition, it overcomes disadvantages and drawbacks of existing olfactory test and sensory stimulation formats because it is fully automatic, more convenient, faster and more precise. Because ink-jet dispensing of airborne materials is precise, discrete, digital, programmable and interactive, the speed and accuracy of dispensing materials to become airborne is several orders of magnitude better than can be obtained by any other method. Moreover, because devices can be made small, the size of the systems can be reduced to a few cubic inches. Since the present invention is controlled by digital electronics, all types of digital computer and interactive control is possible. Many different rates, intensities and combination of airborne materials can be presented at a mere keystroke or switch closure. Because the systems of the present invention can dispense volumes as small as a few tens of picoliters of fluid, they can provide exquisitely fast and precise olfactory inputs near the threshold (approximately 10 billion molecules) of human olfactory.

The miniature size of the devices of the present invention make novel applications possible. The devices can be fitted inside any air handling systems (such as scuba airways, pilot airways, automotive air handlers, etc.), and can be worn (on glasses, helmets, decorative pins, microphone holders, etc.) or can be concealed near objects (in headrests, door jambs, table centerpieces, television chassis, etc.). All of these applications open exciting new horizons to olfactory access not heretofore available. Other patent applications in related art by inventors with an obligation to assign to the owner of the present application are U.S. application Ser. No. 08/837,646, filed Apr. 21, 1997 entitled "Presenting Airborne Materials to the Nose", and U.S. Ser. No. 09/110,486, filed Jul. 6, 1998, entitled "Method and Apparatus for Dispensing Airborne Materials for Controlling Pests, incorporated by reference herein.

An interesting commercial application of the present invention lies in the entertainment field in the installation of a plurality of ink-jet dispensing systems throughout a movie theater and programmed to quickly produce odors synchronized with the film being shown. They can be quickly turned on or turned off under programmed control to enhance the theater going experience.

Finally, the precise control offered by the ink-jet based dispensing system of the present invention can be used as a real time calibration source for electronic sensors which, although in their infancy are the subject of considerable developmental activity as a means for detecting and measuring odors. Calibration of these devices is particularly significant because they are known to drift in response to ambient conditions such as temperature and relative humidity. The reproducible delivery of a known quantity of a known material makes real time baseline calibration possible. In the converse of this, electronic sensors can be used to verify the operation of the ink-jet dispenser where it is important to make sure the dispenser is functioning.

BRIEF DESCRIPTION OF THE DRAWINGS

FIG. 9 is a printhead having a heater attachment so that the printhead temperature can be controlled above room temperature;

FIG. 10 illustrates a fragrance ejection device mounted on a microphone together with a computer monitor and keyboard comprising a control system to synthesize fragrances;

FIG. 11 is an exemplary screen for the system of FIG. 10 whereby settings can be adjusted to vary the percentages of components by operating individual ejection devices of a printhead;

FIG. 23 is a schematically illustrated system for calibrating a sensor array commonly referred to as an "electronic nose";

FIG. 24 is an enlarged view of a portion of the system of FIG. 23 showing the microjet ejecting device and a heated target medium generating a calibration gas;

DETAILED DESCRIPTION OF THE INVENTION

Figure 1:
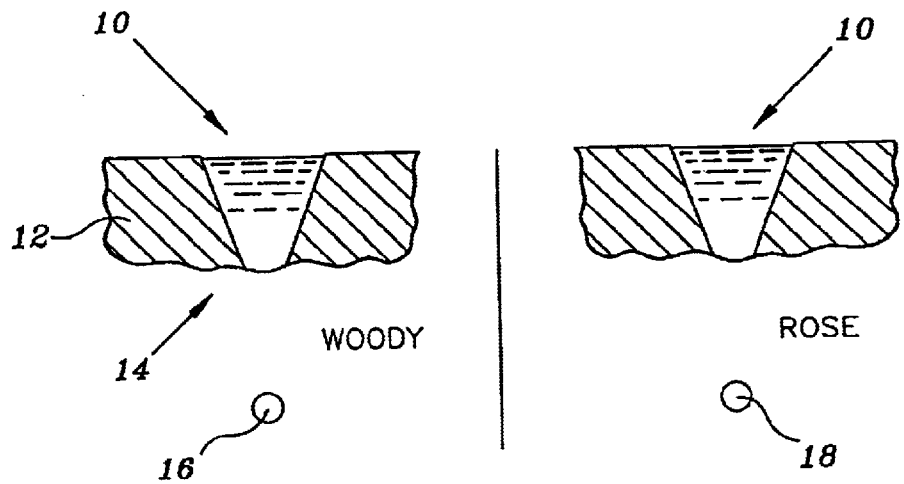
FIG. 1 illustrates an odorous fluid being ejected from the orifice of an ejection device.

In the description that follows, like parts will be referred to by the same name and reference numeral in so far as possible. The invention relies upon the precision dispensing and subsequent vaporization of one or more fragrance, aroma, or odor producing fluids into the air for use in a variety of applications. Airborne materials are microdispensed into inspired airstreams or personal air space of one, two, or more subjects or a testing space. The airborne materials are presented in a form of a substance containing a volatile component.

Table 1A includes a common name of a variety of different materials having volatile components which are readily recognized by the human nose when presented in sufficient concentration. Many other such materials are known which are produced from natural substances or synthesized. Such materials are listed non-exhaustively in Table 1B.

TABLE 1A

| | |
|---|---|
| Peanut | Watermelon |
| Soap | Grass |
| Paint Thinner | Natural Gas |
| Motor Oil | Cinnamon |
| Smoke | Pineapple |
| Lemon | Coconut |
| Menthol | Dill Pickle |
| Onion | Clove |
| Licorice | Banana |
| Wintergreen | Garlic |
| Orange | Peach |
| Lilac | Lime |
| Grape | Leather |
| Gasoline | Gingerbread |
| Bubble Gum | Cheddar Cheese |
| Chocolate | Musk |
| Mint | Cedar |
| Root Beer | Apple |
| Cherry | Black Pepper |
| Strawberry | Chili |
| Fruit Punch | Tomato |
| Rose | Pumpkin Pie |
| Turpentine | Skunk |
| Pine | Whiskey |
| Pizza | Honey |

TABLE 1B

ALDEHYDES - Organic chemicals derived from natural or synthetic materials. Aldehydes add a vivid, quick quality to top notes. Variations can be powdery, fruity, green, citrusy, floral or woody.
AMBER - A fossil resin from the fir tree. Prized for its tenacity, it also adds warm, leathery, powdery elements to a composition. The color amber refers to the color of the resin
AMBERGRIS - Secretion from the male sperm whale, often found floating in the ocean. The Chinese once used it as an aphrodisiac. Ambergris imparts a woody, balsamic odor. Substitutes are used more often today, because the natural substance is difficult to obtain.
AMBRETTE SEED - These plant seeds yield a musky floral, brandy-type aroma.

TABLE 1B-continued

ANJELICA - Oil from the root of the angelica tree, which is cultivated in France, Belgium and Germany. It is musky and peppery, with a spicy green quality.
BALSAM - Tree resins that exhibit a warm, sweet element. They are generally used as a base fixative.
BASIL - A spicy herb with a green impression.
BAY LEAF - A tree leaf valued for its spicy, warm, almost bitter scent.
BAYBERRY - A shrub with berries, from which a waxy substance is taken. Bayberry adds a spicy, woody flair to fragrance.
BENZOIN - Balsamic resin from the tropical styrax tree, used as a fixative, imparting a sweet, coca-like quality. Benzoin is found in Thailand, Vietnam and Laos.
BERGAMOT - Oil produced from the peel of the bergamot fruit. The inedible fruit is of the citrus family and is about the size of an orange. The largest bergamot production comes from Calabria, Italy. The fresh, citrus essence is ideal in top notes and eau de cologne.
BLACK CURRANT BUD - (see Cassis)
BORONIA - Essence taken from the flower of the boronia bush, which is mainly found in Australia. Often used in chypre blends, it leaves a spicy-rosy impression.
BROOM - This produces a sweet, grassy odor. It is derived from the blossoms of the Mediterranean-area Spanish broom shrub.
BUCHU - Substance from the leaves of the buchu herb. It yields a strong minty, camphor odor.
BULGARIAN ROSE - A highly valued flower in perfumery, grown in Bulgaria's Valley of the Roses at the base of the Balkan mountain range, where a Turkish merchant began cultivation centuries ago.
CARDAMOM - Oil distilled from the cardamom plant, a member of the ginger family. It leaves a spicy floral impression. It is second only to saffron as the world's most expensive spice. In India, Cardamom grains are chewed to freshen the breath.
CARNATION - This flower gives off a spicy, sensual aroma.
CASSIA OIL - Obtained from the leaves of an evergreen tree, valued for its spicy cinnamon-like quality. The oil is also used in cola drinks.
CASSIE - Derived from the *Acacia farnesiana* bush, the cassie absolute produces a spicy floral flavor.
CASSIS - Oil taken from the bud of the black currant fruit, which is also used in liqueur.
CASTOREUM - A secretion from the beaver that exudes a leathery quality and is used as a fixative.
CEDARWOOD - Oil obtained from the juniper cedar tree, which is a native to Texas. An excellent fixative, it has a distinct wood tone.
CHAMOMILE - A sweet, herbal odor with fruity notes, often used to balance floral compositions.
CINNAMON - Oil obtained from the bark and leaves of the cinnamomum tree, which is native to Southeast Asia and the East Indies. It imparts a familiar warm, sweet, spicy odor.
CIVET - A glandular secretion from the civet cat, used as a fixative. Repugnant by itself, civet blends well and adds a warm, leathery, erotic tone to a composition.
CLARY SAGE - An herb valued for its sweet, subtle quality.
CLOVE - Obtained from the clove tree, clove buds are prized for their spicy sweetness. The tree is cultivated in Sri Lanka, Madagascar and Indonesia.
CORIANDER - Oil from the coriander herb of the parsley family, valued for its spicy aromatic impression.
COSTUS - Essence from the root of the costus plant of the plant of the daisy family, lends warmth to Oriental blends. It has green, violet-like accents.
COUMARIN - Obtained from the tonka bean and often created synthetically, produces a sweet, herbal, spicy, hay-like odor, similar to vanilla.
CYCLAMEN - Essence taken from the heart-shaped flowers of the primrose family.
EUCLYPTUS - Oil from the leaves of the eucalyptus tree, leaves a strong herbal, camphor impression. Discovered in Tasmania, it is widely cultivated in Spain, Portugal and Australia and is well priced.
FRANGIPANI - Oil from the sweet, jasmine-like flowers of the frangipani tree.
GALBANUM - A gum resin valued for its leafy green, soft balsamic odor. Galbanum is used in many fragrances to provide a pleasing freshness, or green lift.
GARDENIA - A heady white flower with a strong sweet scent.
GERANIUM - Oil made from the leaves and stems of the plant. Depending on the variety, it gives off a rosy, minty or fruity essence often used in rosy or spicy compositions.
GUMS - Resins or balsams secreted from plants. Exhibiting a sweet tenacious odor, they are often used as fixatives.

TABLE 1B-continued

HELIOTROPIN - An aldehyde with a floral almond tone, found in pepper oil.
HONEYSUCKLE - A highly fragrant vine flower but difficult to capture correctly. The essence of the honeysuckle is usually re-created by blending a variety of florals.
HYACINTH - A sweet floral that imparts a green impression.
INCENSE - Made from gums and resins, produces a spicy aroma when burned.
JASMINE - Called the king of flowers, a sweet tiny white flower with a vibrant, smooth aroma. Jasmine is one of the most prized essences in the perfumer's palette. It is grown in France, Morocco, India, Egypt and Spain and must be harvested before sunrise to retain the full amount of its delicate fragrance.
JONQUIL - Highly fragrant essence derived from a flower of the narcissus family, rare because it is difficult to distill.
LABDANUM - A dark resin obtained from the rockrose herb, valued for its leathery odor.
LAVENDER - From the flowering tops of lavender plants in France, Spain, Morocco and old Yugoslavia, a sweet, light essence with woody floral accents. The oil is used in lavender waters, chypres, fougeres and florals. Lavender water is said to have been a favorite of Madame de Pompadour, mistress of Louis XV
LEATHER - A smoky, sweet, animal odor crafted from the perfumer's palette. It is warm and persistent.
LEMON - Oil from the lemon rind. It is a zesty, sharp, refreshing essence, and is added to brighten many compositions, particularly eau de cologne.
LILAC - Since the essence released by the lilac plant and flower does not accurately portray its aroma, the perfumer re-creates the essence by using jasmine, ylang-ylang, neroli and vanilla.
LILY OF THE VALLEY - Also known as muguet, lily of the valley is invented by the perfumer, using jasmine, orange blossom, rose, ylang-ylang and chemical additives. The sweet essence is difficult to obtain from the natural flower.
MAGNOLIA - A sweet, highly fragrant flower, also stubborn in releasing its essence. The perfumer re-creates the essence by blending rose, jasmine, neroli and ylang-ylang with aroma chemicals.
MANDARIN - Oil from the peel of the mandarin orange fruit, a brisk, sweet essence often used in eau de cologne.
MAY ROSE - Also called rose de mai. The May rose from Morocco produces a rich, long-lasting oil prized for its full-bodied, diffusive qualities.
MIMOSA - A green floral essence obtained from mimosa green flowers and stems. It imparts a smooth, sweet aroma.
MOSS - Earthy essences are derived from a variety of mosses: oakmoss, treemoss, lichen, seaweed and algae.
MUSK - A glandular secretion from the male musk deer from Tibet, China and Nepal, used as a fixative in fine perfumes. It is valued for its woody, animal, erotic impressions, though nowadays it is often created chemically by the perfumer. Soft, sensuous, pervasive.
MUGUET (see Lily of the Valley)
NARCISSUS - A highly fragrant yellow and white flower that produces an intense spicy, earthy and sweet straw-like odor. Small amounts are often used to round off floral compositions. Native to Persia, the narcissus flower was carried to China over the silk route in the eighth century.
NEROLI - Made from the orange blossoms of the bitter orange tree grown in France, Egypt, Algeria and Morocco. It is light, sweet and spicy and is used in top notes and eau de cologne. It was named for the Duchess of Nerola and was often used to scent gloves.
NUTMEG - Spicy oil derived from the seeds of the South Asian nutmeg tree.
OAKMOSS - A lichen grown on oak trees. Its odor is earthy, woods and slightly leathery. It is used as a fixative in many blends, especially chypre.
OLIBANUM - Also called frankincense. Olibanum is a gum resin from a tree found in Africa and Saudia Arabia. A fixative, its odor is spicy and balsamic, similar to odor of incense.
OPOPANAX - Derived from a gum resin and is similar to myrth. A woody, sweet fixative.
ORANGE OIL - Produced from the peel of the orange, and often used in eau de cologne and floral fragrances. Refreshing, sweet, fruity and crisp.
ORANGE BLOSSOM - From the white blossoms of the bitter orange tree. It adds a warm, spicy flavor that is often used in floral compositions.
ORRIS - One of the most expensive ingredients used in perfumery. It is obtained from the iris plant, which is commonly cultivated in Italy. Its odor is violet-like and can be warm, sweet, woody, fruity or floral, depending on the quality.

TABLE 1B-continued

OSMANTHUS - Produced from the flowers of the osmanthus tree, which is found in Japan, China and Southeast Asia. It has a floral odor, with a hint of plum and raisin.
PATCHOULI - Oil obtained from the leaves of the patchouli plant, a superb fixative. Discovered in India, it is also cultivated in Malaysia and Indonesia. Its odor is earthy, dry, woody and spicy. Patchouli is often used in Oriental and chypre blends.
PETITGRAIN - Essence derived from the leaves and stems of the bitter orange tree. It has a subtle woody tone similar to neroli. Sweet and floral, petitgrain and freshness to a fragrance, especially eau de cologne.
RESIN - Gum secretions from trees and plants, often used as fixatives.
ROSE - Rose oil is also referred to as "otto" or "attar" of rose; these terms refer to perfume oil produced through distillation. There is a wide variety of roses, and the rich oil they produce has the familiar rose aroma, though undertones vary from honey to fruity, spicy to musk, and violet to green. Called the queen of flowers, it is one of the most precious ingredients in perfumery. Roses bloom just thirty days of the year and must be picked quickly, for they lose half their essence by noon. Centifolia and Damascena are popularly cultivated roses. The floral essence is used in rose water, floral, chypre and Oriental compositions. Rose water was said to have been a favorite of Marie Antoinette.
ROSEMARY - Flowers and leaves of the evergreen rosemary herb of the mint family, distilled for use in perfumery. The oil produces an herbal note that is woody and slightly lavender-like.
ROSE DE MAI (see May Rose)
ROSEWOOD OIL - Oil obtained from the wood of the rosewood tree, the *aniba rosaeodora* of the laurel family.
SAGE - A fresh, spicy odor from the sage herb.
SANDALWOOD - Oil from the sandalwood tree, the evergreen *santalum album* grown in india, Australia and Southeast Asia, though the Indian province of Mysore supplies 85% of all sandalwood. The wood is valued for its aroma and its imperviousness to termites. The trees must mature at least thirty years for the oil to fully develop. An expensive ingredient, sandalwood oil is prized for its fixative quality. Its odor is powdery, balsamic, wood and rich. Sandalwood gives a smooth finish to Oriental, chypre and floral perfumes.
STYRAX - A sweet balsam found on the styrax tree, an excellent fixative
SWEET PEA - A flower oil produced from the fragrant flowering vine, valued for its light, delicate nature.
TAGETES - Essence produced from the tagetes flower, which is grown in Spain, Italy and South Africa. The strong essence has an herbal, aromatic personality with fruity undertones
THYME - Derived from the flowering herb. Thyme smells sweet and herbaceous - ideal for eau de cologne.
TONKA BEAN - Fragrant seeds from native South American trees of the Dipteryx family.
TUBEROSE - One of the most expensive oils, from a flower known for its rich, sensual aroma. Its cost is due in part to a painstaking processing called enfeurage, then the oil is separated with alcohol. Tuberose is a perennial plant native to Mexico. The sweet, honey-like aroma adds to fullness to many floral fragrances and blends well with gardenia, jonquil and hyacinth.
VIOLET - The violet flower yields such a minute amount of oil that it is cost prohibitive to extract. Instead, the violet aroma is created chemically for use in perfumery.
VANILLA - Made from the fruit and seeds of a climbing orchid vine. It has pods, or capsules encasing the beans. Vanilla is an impressive sweet fixative, used in many Oriental, amber and floral perfumes.
VANILLIN - Can be produced naturally from the vanilla pod, and from certain balsams and benzoins. It can also be made synthetically. Its sweet, strong odor is similar to vanilla, but lacks the depth of vanilla. Vanillin blends well with vanilla to produce a round, full-bodied vanilla aroma.
VETIVER - A grass grown in Haiti, Reunion Island, Brazil, China and Southeast Asia. It has a woody, earthy quality, enhanced by a moist balsamic accent. A superb fixative vetiver is an important component in chypre blends.
VIOLET LEAF - Oil from the leaves of the violet plant, valued for its cumcumbery green and peppery herbal aroma, with touches of violet and iris. Parma, Italy, is known for its violet production.
YLANG-YLANG - From Tagalong for "flowers of flowers." This oil comes from the flower of ylang-ylang trees grown in Madagascar, Indonesia, Comoros and the Philippines. The rich oil has a jasmine-like aroma and sweet balsamic accents. used in many floral and Oriental compositions. Ylang-ylang smooths and rounds bitter notes, adding warmth and grace.

FIG. 1 is a representation of an actual photograph of an ejection device denominated 10 showing only a portion of the nozzle 12 having an orifice 14. The orifice 14 is normally conical in shape as shown, tapering forward to the smallest diameter where a liquid meniscus is present from which the droplets emerge. Two different liquids are shown being ejected from jetting device 10. A droplet 16 of the fragrance Woody is shown on the left and a droplet 18 of the fragrance Rose is shown on the right. Many different fluids can be dispensed with similar results. A large number of such fluids have been demonstrated and are referenced in the background section of this application. The droplet sizes in FIG. 1 are approximately 60 micrometers although the creation of droplets for this technology range from droplets having diameters of about 10 micrometers to over 350 micrometers in diameter. Droplet sizes can be varied by altering the signals provided to a single device as demonstrated in U.S. Pat. No. 5,461,403 which is incorporated herein by reference. While the Woody and Rose droplets are being sequentially produced with individual ejection devices 10, it is evident that the method can simultaneously eject these components at the same or different rate to produce a "Woody-Rose" combined fragrance.

Figure 2:
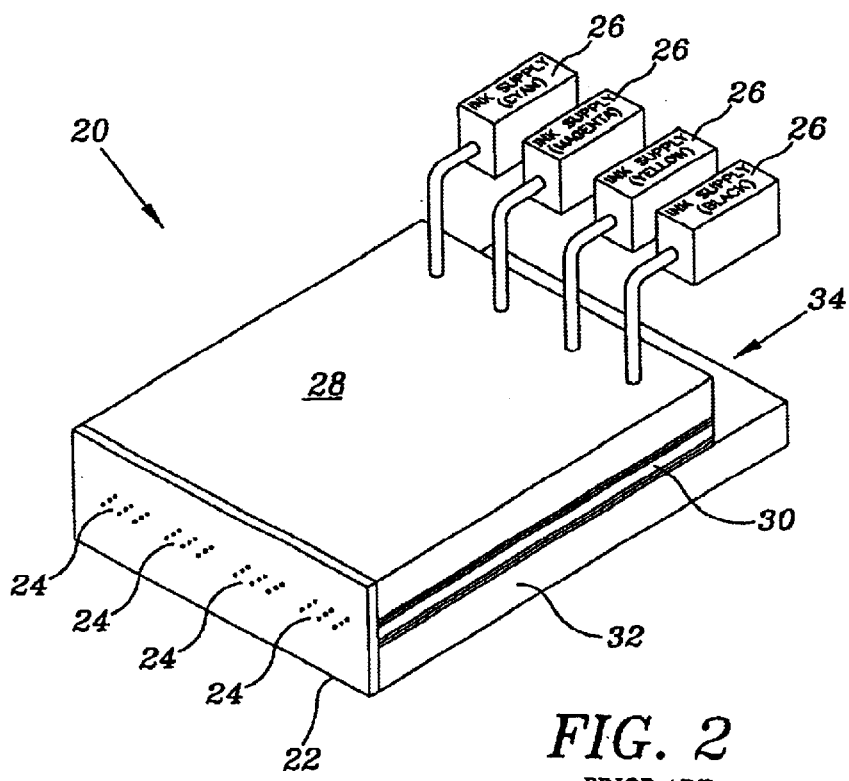
FIG. 2 schematically represents a four fluid, multi-jet printhead of the type commonly used for ink-jets.

FIG. 2 schematically illustrates a multi-fluid printhead 20. The front of printhead 20 has an orifice array 22 having four multiple orifice regions 24, each of which is for a different fluid. Each of four fluids are supplied by four individual fluid reservoirs 26 which pass through between upper body 28 and main body 32 of device 26 to supply fluid to channels 30, which can be controlled separately to eject fluid on demand. Layers that form the channel are seen on the side of device 20 but the channels themselves are hidden within the area between the upper body 28 and a lower main body 32. The back end portion 34 supplies electrical connections to drive the printhead 20. Main body 32 of this particular printhead is made of piezoelectric material called PZT. The PZT is the actuator material that drives the printhead. This type of construction is disclosed in U.S. Pat. Nos. 5,208,980, 5,227,813 and 5,402,162 which are incorporated herein by reference. Although this type of printhead has channels actually cut or formed in blocks of PZT material, it is evident that individual ejection devices 10 can be combined in the manner indicated in FIG. 5, where the "channel" is an individual tube connected to a reservoir to supply the volatile fluid for ejection. It should be understood herein that the term printhead comprehends both such types of devices.

Figures 3, 4:
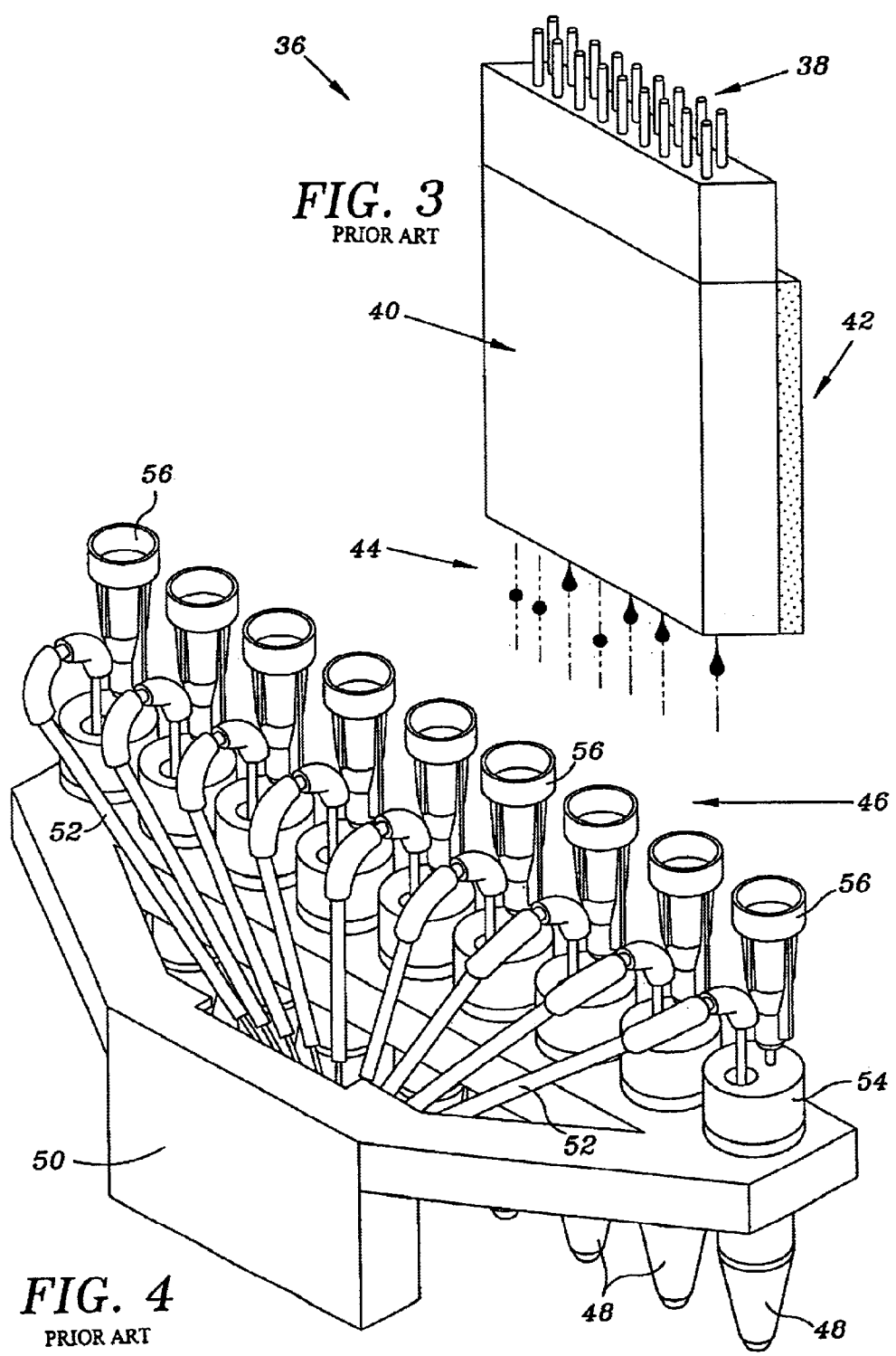
FIG. 3 represents a multi-fluid jetting device with an electrical interconnect on the side.
FIG. 4 represents a multi-fluid jetting device with fluid reservoirs and support hardware.

FIG. 3 schematically discloses a jetting device 36 for ejecting multiple fluids in a slightly different configuration and with eighteen different fluid inputs 38. The device has a PZT body 40 with an electronic connection 42 shown as an interconnect substrate on the underside of printhead 36. Printheads of this type are disclosed in U.S. Pat. Nos. 5,435,060 and 5,666,145 which are incorporated herein by reference.

FIG. 4 is an ejection device 46 similar in construction to FIGS. 2 and 3, showing a plurality of larger fluid reservoirs 48 can be arranged in fluid communication with a smaller printhead mounted in a support structure 50. A plurality of tubular connections 52 connect the inlet to the printhead of fluid reservoirs 48 through fluid reservoir covers 54. A plurality of connectors 56 are shown for loading fluid into reservoirs 48. The specific sizes and materials for use in contact with the variety of fluid components to be dispensed is within the knowledge of someone skilled in the art. Although only nine fluid reservoirs are shown, ejection systems with many more fluid reservoirs could be used. Fluid can be pre-filtered before loading them into the reservoirs or small filters can be installed between fluid reservoirs 48 and the printhead 46.

Figure 5:
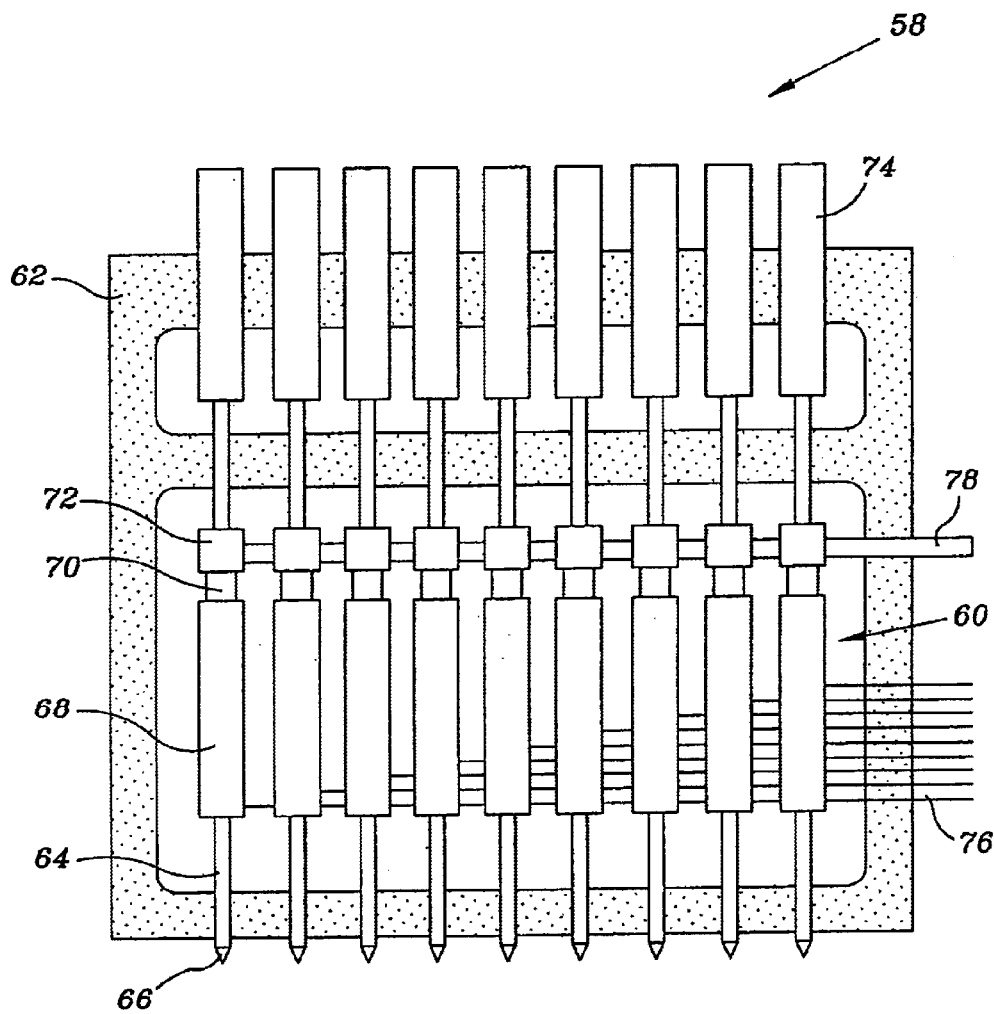
FIG. 5 represents a printhead made with an array of single jet devices, each with its own fluid input.

FIG. 5 illustrates a printhead 58 containing nine single ejection devices 60 mounted in support structure 62. Devices 60 comprise a glass tube 64 with an orifice 66 at the end. Glass tube 64 is bonded to a piezoelectric element 68 covered with an electrode layer. The piezoelectric element is exposed at a small section 70 that separates the electrode from another electrode 72 which extends around the end of the piezoelectric element and covers the inside of the piezoelectric tube element 68. Plastic tubes 74 are connected to the ends of the glass tubes 64 farthest from the orifice. Plastic tubes 74 would connect to fluid reservoirs (not shown). Metalization on the outside of the piezoelectric material is connected to independent leads 76 which allows each device 60 to be fired separately. The common electrical connection 78 is connected to electrodes 72 which electrically connects the inside of the piezoelectric tubes. The devices shown in FIGS. 2, 3, 4 and 5 are shown to reveal variation of the printhead design and types of fluid and electrical elements; but in no way should it limit the invention to these specific designs. This type of design is illustrated by U.S. Pat. No. 5,053,100 and U.S. Pat. No. 5,681,757 which are incorporated by reference herein.

Figure 6:
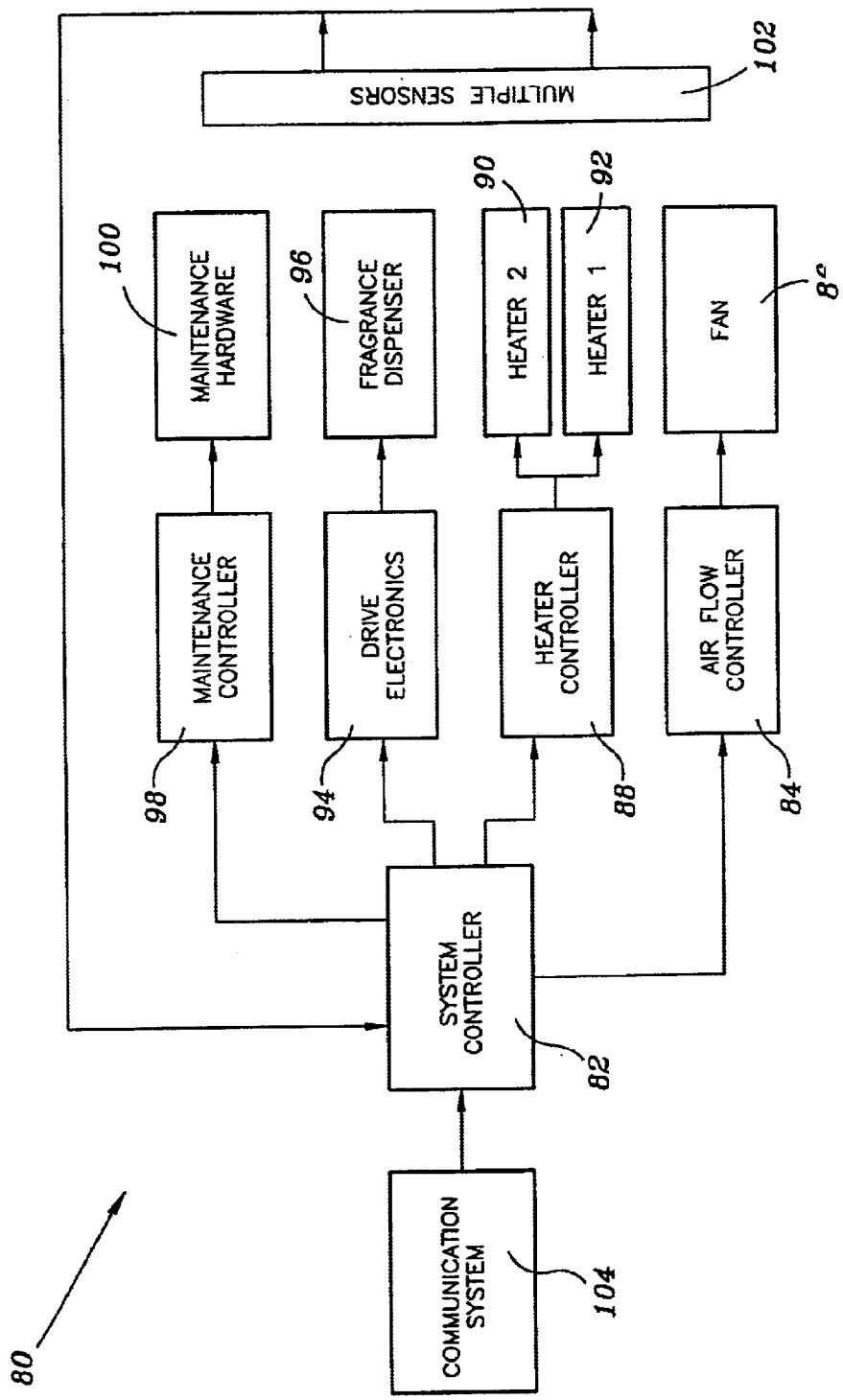
FIG. 6 is a block diagram of the control system for a fragrance ejection device.

FIG. 6 illustrates schematically a block diagram for a control system 80 for a complete fluid ejection system. Not all elements shown in the diagram may be present in every system, but their presence will depend upon the particular application. System controller 82 may be programmed to send signals to airflow controller 84 which controls an air movement device 86 which may comprise a fan or blower or compressed gas. Controller 84 could be nothing more than a switch to turn off a blower 86. Heater controller 88 also under control of system controller 82 may control power to one or more heaters 90, 92 comprising heatable surfaces used in the system. The location and types of heaters will become clear from further discussion in connection with the applications. Drive electronics 94 creates the voltage pulses that drive the piezoelectric actuator of the dispenser or dispensers 96. System controller 82 may be programmed to signal drive electronics 94 to deliver or to terminate certain types of pulses necessary to fire one or more individual ejection device and may download the voltage wave form to the drive electronics in connection with this task. Maintenance controller 98 and maintenance hardware 100 may be included for the purpose of keeping the ejection device or devices functioning. For example, it may wipe the orifice array on command from the system controller. In many applications it will not be necessary. Sensors 102 may be used with the system to monitor a specific parameter and feed back information representative of the parameter to controller 82. For example, one type of sensor 102 could monitor the temperature of a specific location, for example the heater temperature or the ejection device temperature. Another type of sensor could monitor the vapor density or relative humidity in the ejection area. FIG. 6 shows the sensors 102 feeding back information to the system controller. It could feed information back to an individual element controller. Communication system 104 may be used to feed command signals to system controller 82. This could be as simple as a switch or it could include inputs from a computer system. Other types of communication devices 104 could be radio signals, a network connection, a motion sensor, etc. The system controller and communication system can be combined into one unit.

Figure 7:
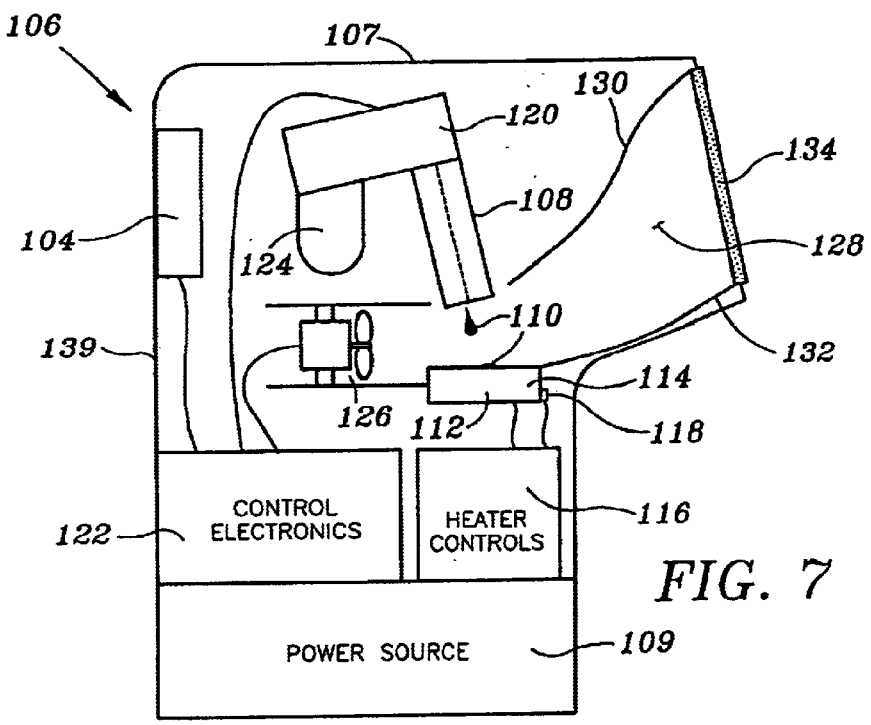
FIG. 7 schematically illustrates a fragrance ejection device with a heated target, air-flow, and control components, with the side cover removed.
Figure 8:
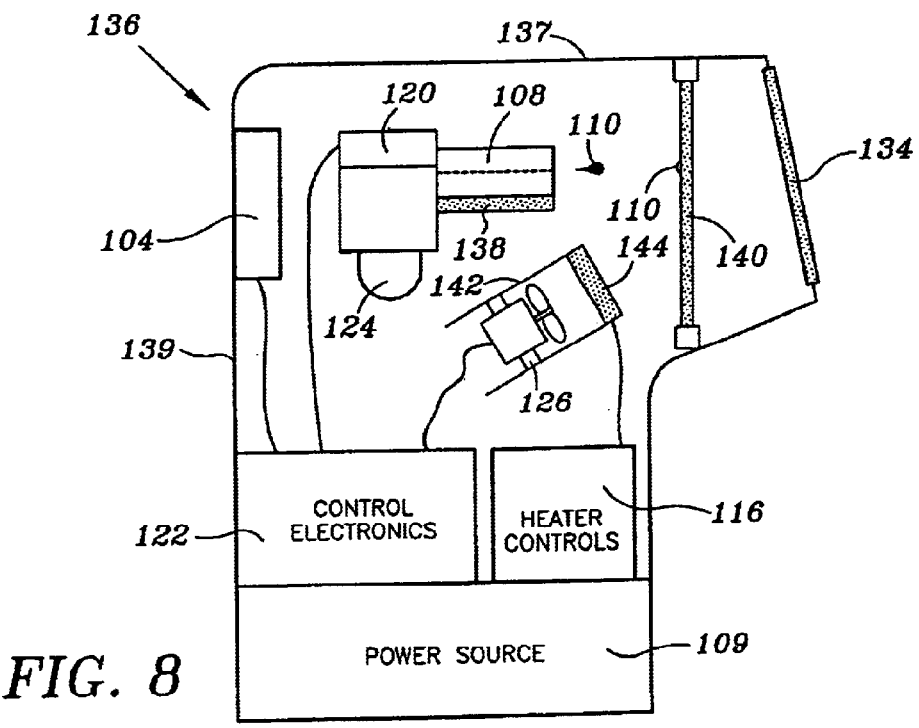
FIG. 8 is an alternate fragrance ejection device including a flow-through target and the use of heated air.
Figure 12:
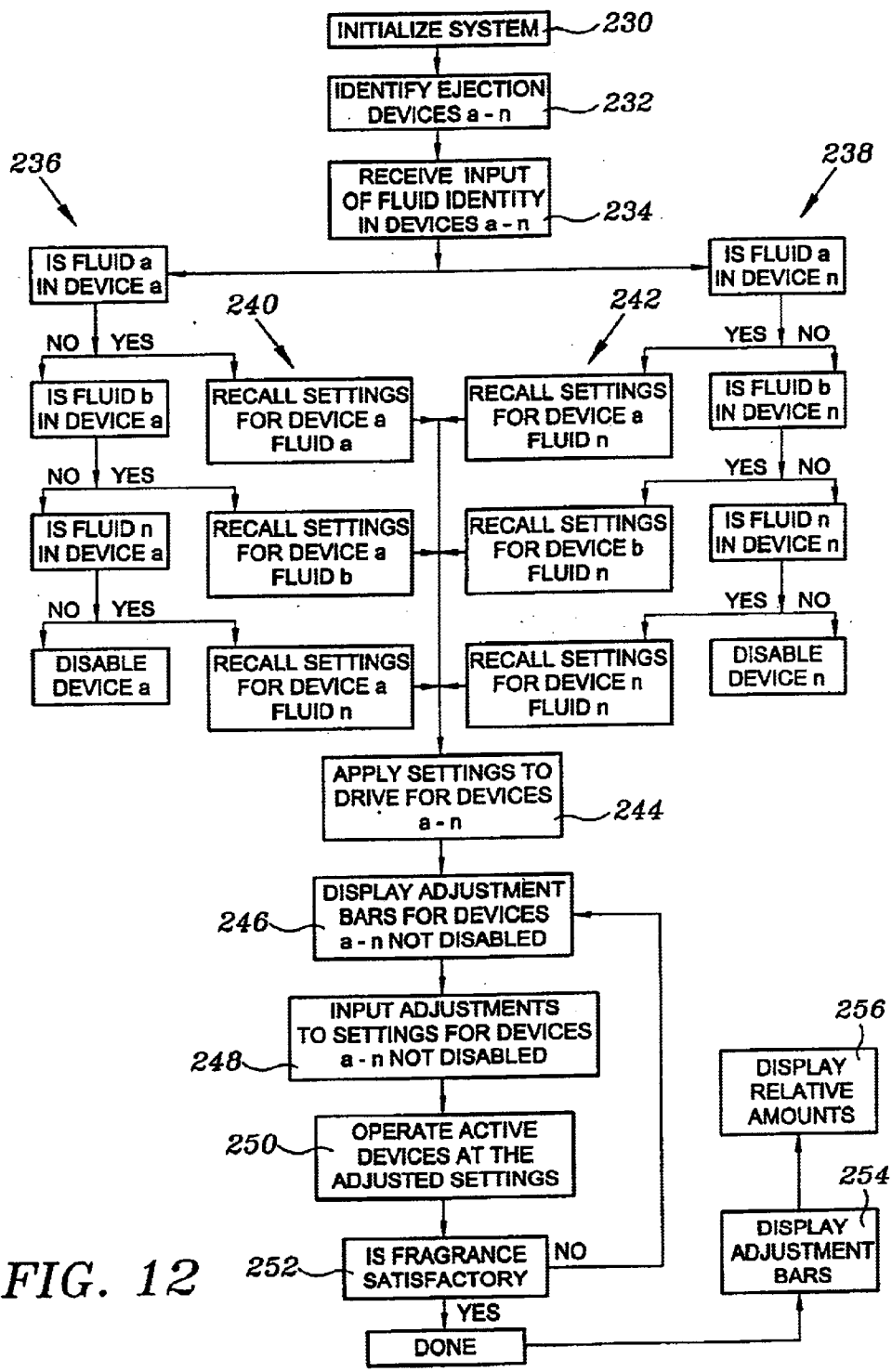
FIG. 12 is a high level flow chart for the fragrance synthesizing system illustrated in FIGS. 10 and 11.

A fragrance ejecting device 106 is schematically illustrated in FIG. 7 as containing many of the elements of FIG. 6. It is mounted in a housing 107. Power source 109 for the device may be a battery for mobile devices. Printhead 108 could be a printhead like the printheads disclosed in the previous figures or a printhead comprising a single ejection device. Printhead 108 dispenses droplets 110 onto a heated surface 112 of a heater 114. Heater controller 116 monitors the signal from temperature sensor 118 to control the surface to a set-point by adjusting power to the heater.

Printhead 108 is driven by drive electronics 120 which receives control signals from system controller 122. Fluid to be jetted is stored in reservoir 124 in fluid communication with the ejection element of printhead 108 through a capillary. Blower 126 creates air-flow which carries vapor through an air-flow channel or passageway 128 bounded by surfaces 130, 132. Air/vapor may pass out of the device through airflow outlet 134 which may be provided with a grating or permeable cover. Although the device has been shown as having a powered air movement device, it should be understood that in some cases convection or diffusion may be used to transmit air/vapor out of the device in which case a blower might not be needed. A temperature sensor might not be used in some cases where the heater is controlled simply by a specified resistance and voltage. Therefore, not all elements discussed in FIG. 7 need be used for a fragrance ejection device. It should also be understood that the printhead can have more than one orifice and more than one fluid can be provided with reservoirs and orifices appropriate to the number of fluids to be dispensed. The signals from the control electronics determine which fluids are jetted, the number of drops of each fluid being jetted and the timing of jetting of the various fluids. This information is either programmed in the control electronics or downloaded from another intelligent system.

Low mass heaters are an important aspect of the apparatus because they allow quick evaporation of volatile fluids to generate enough vapor to produce the desired odor sensation and just as quickly cool off to stop it when the heater is used as a target medium. Another characteristic of heaters for this invention is that they do not produce an odor when heated. This is both critical and difficult to achieve. In addition, the target surface of a heater must allow wetting so that droplets do not bounce off the surface but wet it instead. A ceramic cement which wetted well, had no odor of its own after a little burn in time and withstood the heat is available through Cotronics Corp., Brooklyn, N.Y. identified as Durapot 801 is rated to 1650° C. The cement desirably enhances surface roughness of the heater which greatly improves wettability. It is also contemplated that surface roughness to improve wetting could be provided to the heating surface of the heater (impact surface) by such means as sand blasting, wire brush, sanding, ablation or other forms of abrasion.

Two types of heaters that worked well are surface mount resistors and thin film devices including platinum resistance temperature devices (RTD's). Surface mount resistors are rugged, inexpensive and readily available in a wide range of resistance values. Experimentation will readily determine the best resistance value for a particular temperature. If temperature control is desired, the RTD's are preferred. They are available through Omega Engineering, Stamford, Connecticut as part number TFD. Any of their thin film devices are useable. TFD's which had a resistance of 100 ohms and range of 100 volts D.C. were operated around 24 volts. Using RTD's at temperatures above the melting point of solder is possible as the leads are attached to allow temperature of 550° C. The temperature to evaporate phenethyl alcohol, for instance, was around 240° C. This is a useful solvent for fragrance dispensing.

To implement temperature control, a temperature sensor is best used with the heater. A preferred arrangement is the combination of two TFD;s or similar RFD;s mounted back to back with a high temperature silicone rubber cement. One RTD is then used as a heater while the other is used to sense temperature for feedback to the system controller in a rugged compact arrangement. If the temperature to be used to evaporate droplets is low enough, then the heater RTD may be replaced with a surface mount resistor at a significant cost savings. Other means to generate heat are contemplated including wire resistance heaters, laser radiation, etc.

FIG. 8 schematically shows another configuration of a fragrance ejecting device 136 in housing 137 which may include air inlet 139. Most of the elements are the same as those of device 106 from FIG. 7. Discussion of the common elements will not be repeated. Printhead 108 differs in this embodiment in that it includes an electrical interconnect 138 on the bottom of the printhead and the drive electronics 120 have been located in the different position. A significant difference in the construction of device 136 is the presence of a target medium 140 which intercepts droplets 110 as they are directed toward outlet 134. Target medium 140 in this instance is preferably a permeable medium suitable for disbursing the volatiles, for which an exemplary material may be cloth. Other materials such as a fine wire mesh or perforated metal or ceramic disk might be conducive to providing a heating means for the target medium. Blower 126 is an air movement device mounted in a housing 142 containing a heating element 144. This assembly warms and heats the air being moved which together with the vapor produced by evaporation of drops 110 proceed through target medium 140 to air-flow outlet 134. In another embodiment, target medium 140 itself could comprise the air-flow outlet by removal of the portions of the housing that extend beyond it or it could be moved flush against the opening 134 where grating 134 is now present. Still further, the printhead itself could be separately heated to raise the vapor pressure of the fragrance or fragrances being dispensed. FIGS. 7 and 8 are but two examples of fragrance ejecting devices based upon the principle of the invention. One skilled in the art can understand that these basic elements can be combined in further different ways and in different shapes and combinations to create additional and different fragrant ejecting devices for other applications.

FIG. 9 schematically illustrates the type of printhead 36 illustrated in FIG. 3 mounted on a support structure 146 which shields the heater 150 and can be used to mount the printhead. The electrical interconnect substrate 42 is shown on the opposite side of printhead from the support structure. Solder joints or leads 148 would be used to electrically mount the printhead assembly. Heater 150 is attached to the side of the printhead.

FIG. 10 shows a small fragrance ejection device 152 mounted on a microphone support arm 154 having a microphone 156 supported on stand 158. An electrical cable 160 is used to attach microphone 156 and ejection device 152 to a computer 162. Computer 162 is conventionally attached to a keyboard 164 and monitor 166. Microfabrication technologies allows for very small fragrance ejection devices to be built. Although the input device is shown to be keyboard 164, one skilled in the art would recognize that other types of communication methods could be used, such as voice recognition, touch screen, remote cellular means, etc. Future video games and virtual reality systems could benefit from a fragrance ejection device, which adds one more human sense to the experience. Ejection device 152 could contain a printhead such as printhead 36, 58 and some or all of the components of the embodiment of FIGS. 7 and 8.

The system of FIG. 10 is continued in FIG. 11. FIG. 11 illustrates a method of synthesizing a custom aroma, in this case involving the possible combination of eleven different fragrances displayed on monitor 166. A multiple fluid printhead 152 is provided having a plurality of electronically operated fluid droplet ejection channels and a fluid supply reservoir for each channel. Computer 162 is programmed to operably drive the electronics connected to printhead 152 and selectively operate the ejection channels at a selected rate to eject droplets into a testing space which in this case may be the outlet 168 of device 152. The multiple fluid supply reservoirs are supplied with each of the desired ingredients shown on monitor 166, or some other combination. Software is provided to operate the selected fluid ejection devices according to the adjustable settings shown on the monitor. Droplet rate production is displayed on monitor 166 along with a percentage indicative of the relative amounts of the different ingredients. The operator can create a desired aroma for personal use or develop a custom aroma in real time by adjusting the settings and ingredients which are selected. Ejection device 152 does not have to be installed on the microphone as illustrated, but instead may be a separate unit presenting ejected droplets in a testing space which may have an opening for a target surface such as a card. Droplets deposited on the card when withdrawn can be sensed by the human nose. The application illustrated on monitor 166 in FIG. 11 actually comes from a famous Paris perfume composition.

FIG. 12 is a high level flowchart for the custom synthesizing system illustrated in FIGS. 10 and 11. This system includes a plurality of fragrance ejection devices 152 each of which has a reservoir which is loaded with a natural or artificial fragrance producing volatile fluid component such as the components listed in FIG. 11. Depending upon the material, they may be neat fluids or dissolved or diluted with a commonly used alcohol composition which has no perceptible odor. The system is initialized in block 230 to identify ejection devices a–n in block 232. The unit is powered up and heaters, if any are used, may be activated. The user inputs the identity or a code representing the identity for the fluid put in the fluid reservoir of each of the devices a–n in block 234. The program tests each device a–n in block groups 236 and 238 to determine according to the instructions provided in block 234 whether a particular device A, B, C, etc. has been loaded with fluid a–n. If it is determined that a particular fluid is loaded in a particular device, the operating settings for operating the ejection device are recalled and made ready for use in group blocks 240 and 242. These settings would include the pulse parameters and frequency for operating each ejection device a–n. The settings are applied to the drive for devices a–n in block 244. Heaters, if used, would also be set here according to the requirements of the particular fluid. Next adjustment bars are display in block 246 on monitor 166. The user inputs adjustments to the settings for the active devices in block 248. Moving the selection bars changes the frequency and/or voltage to be applied to the ejection devices and some measure of the relative amounts that will be dispensed is presented to the user on the screen on the form of the number of drops per second and/or the relative percentage compared to the other fragrance components. In block 250 the devices are operated at the adjusted setting and fragrance tested either by means of the human nose or an electronic chemical sensor (electronic nose) in block 252. Some indication of the fact that dispensing is underway is preferably indicated. If the fragrance produced is satisfactory, the system redisplays the adjustment bars and actual relative amounts dispensed in blocks 254 and 256 so that the user will get feedback as to the final mix. If the fragrance is not satisfactory, the system returns to block 246 and the process continues until a satisfactory fragrance is obtained or the system is shut down.

Figure 13:
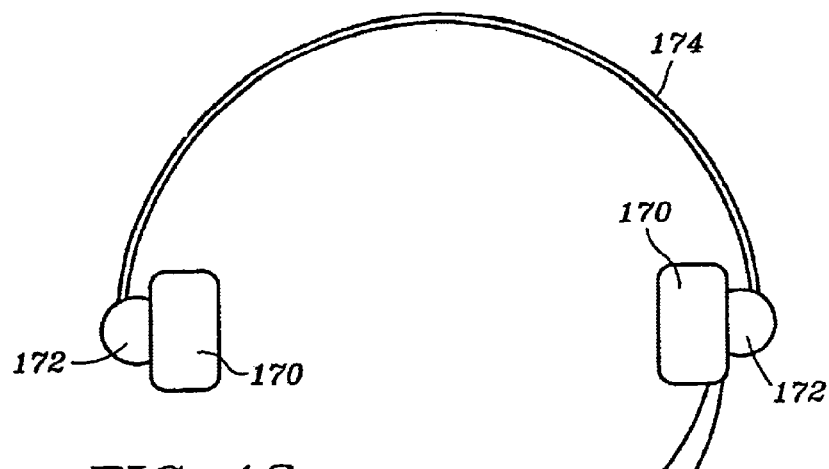
FIG. 13 is a headset with a microphone having a fragrance ejection device mounted thereon.
Figure 14:
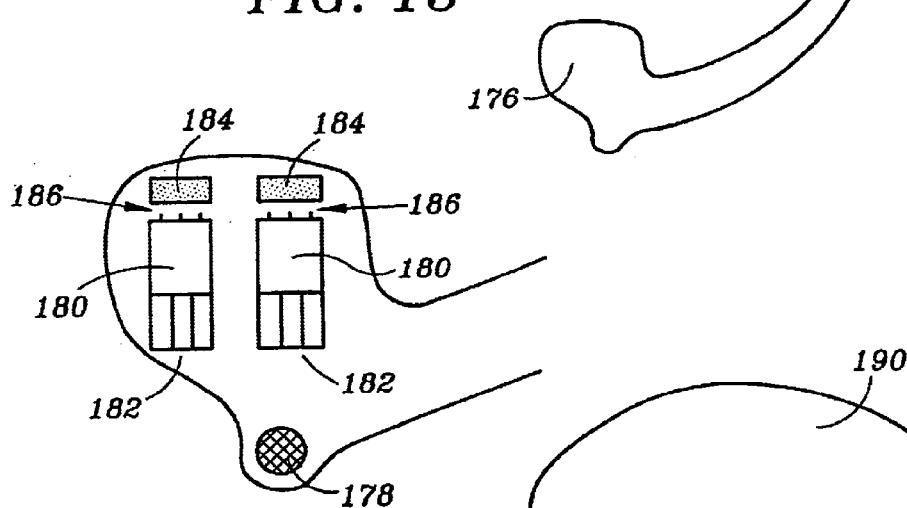
FIG. 14 is a schematic enlargement showing the components inside the mouthpiece of the headset of FIG. 13.
Figure 15:
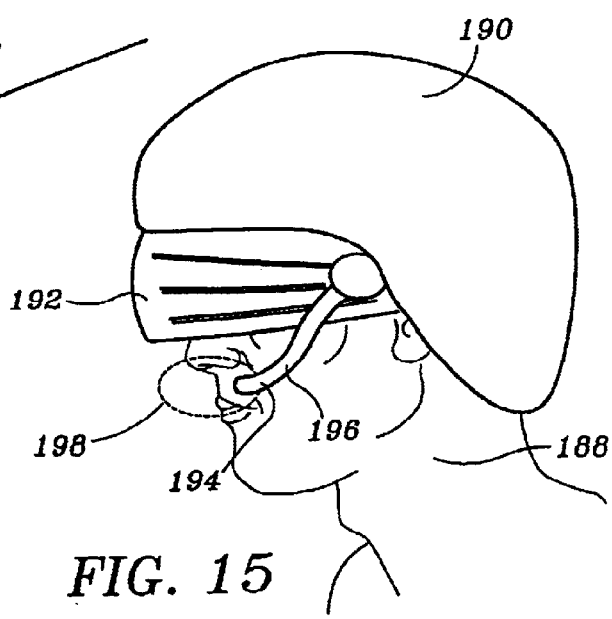
FIG. 15 illustrates how a virtual reality head-set can include a fragrance ejecting device to enhance the experience.

FIGS. 13 and 14 illustrate another application of fragrance ejection devices mounted in the housing of microphone 176. A support band 174 having brackets 172 carry earphones 170. FIG. 13 schematically illustrates the contents of microphone element 176. In addition to microphone 178 are two fluid ejection devices 180 which are multiple ejection devices having multiple fluid reservoirs 182. Heaters 184 serve as a target medium for multiple orifices 186 of devices 180. The power supply, controllers and communication system, if any, are not shown and would preferably be externally connected through wires to devices 180. Such a system could be useful in video gaming or a virtually reality headset whereby ejection of a relevant aroma (smoke, gunpowder, rain, etc.) could be initiated and terminated at different points in the program. The microminiaturization of these devices makes it possible to put a large number of them in a small space ideally suited for such simulations heretofore impossible. For example, virtual reality is illustrated in FIG. 15 where a person 188 wears a helmet 190 containing a virtual reality vision system 192 and a sound system (not shown). The fragrance ejection system 194 is mounted inside an adjustable arm 196. A cloud 198 of fragrance has just been ejected.

Figure 16:
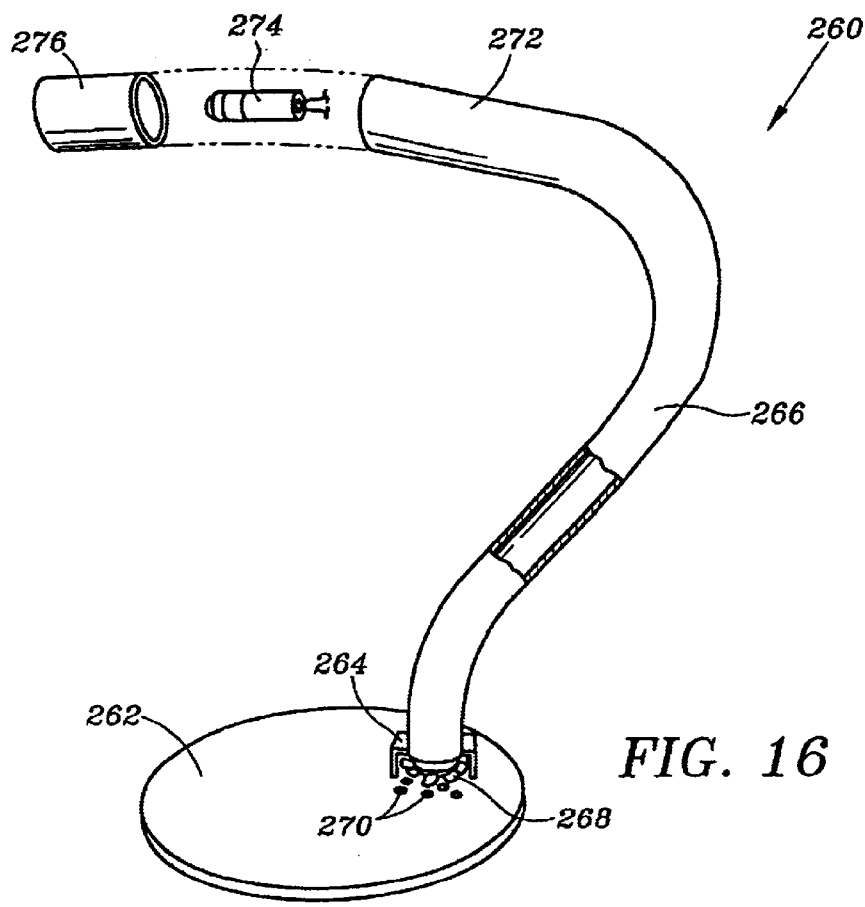
FIG. 16 shows a fragrance dispensing stand with an ejection device and a remotely located blower exposed for viewing.
Figure 17:
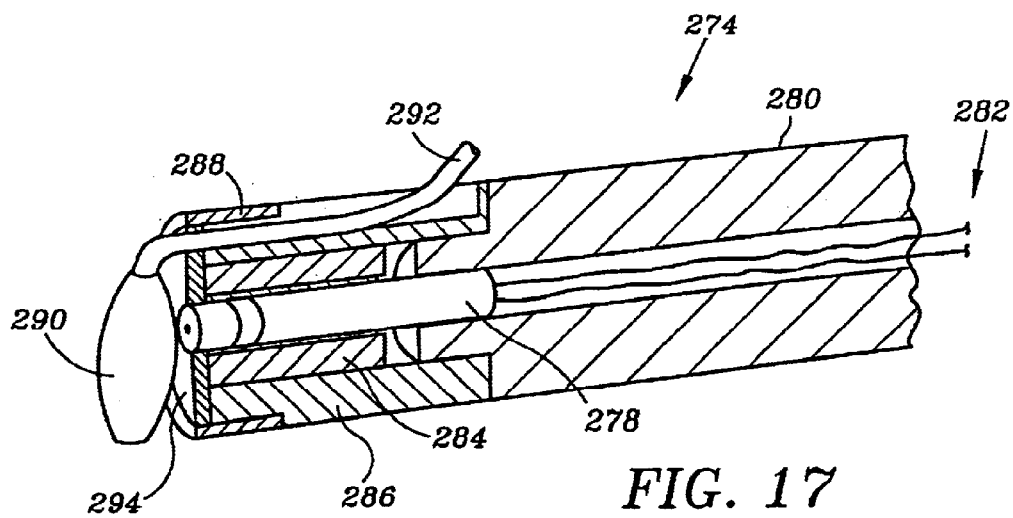
FIG. 17 is an enlarged cut away view of the ejection device assembly from the fragrance dispensing stand of FIG. 16.

FIGS. 16 and 17 represent the components of a fragrance dispensing stand 260 comprising a base 262 having support brackets 264 which support hollow tube 266 on base 262. Blower 268 is mounted on the base in cooperation with a series of openings for air 270. The blower and bracket would be provided with a cover (not shown). In the upper end 272 of tube 266 is a fluid ejection device assembly 274 mounted in spaced arrangement within upper end 272 including a hood 276 which covers the device 274 and has an opening for the emission of air moved past the ejection device.

FIG. 17 is an enlarged view of ejection device assembly 274 which includes a jetting device 278 made integral with a fluid reservoir and mounted in a base block 280 which has an opening for leads 282 which are used to operate the ejection device. The drive electronics and controller could be remotely located and are not shown in this case. An inner spacer 284 and an outer spacer 286 support ejection device 278 on base block 280. A collar 288 supports a target medium 290 comprising a heater having a lead 292. An endplate 294 completes the assembly. This provides an integral unit of very small size which is easily hidden in structures and driven by remote control or through wires that cannot be seen. For example, the device could be surrounded by a bouquet of artificial flowers to create an aroma by operating steadily or intermittently when a light switch is turned on or a motion sensor is activated. Despite the small size, the ejection device 278 can self-contain a large enough quantity of volatile fragrance containing fluid to last a number of months without refilling. The relatively inexpensive cartridge 278 can be removably replaced as a unit much like ink jet printer cartridges.

Figure 18:
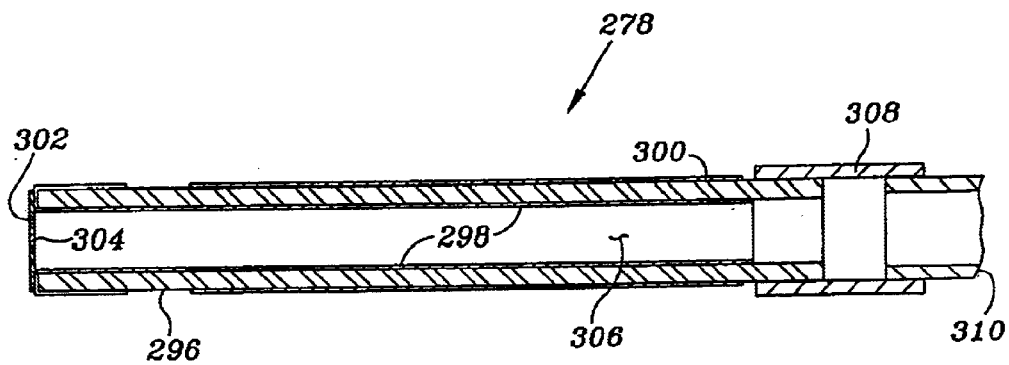
FIG. 18 is a cut away view of a preferred form of the ejection device used in the ejection device assembly of the fragrance dispensing stand of FIGS. 16 and 17.

An exemplary jetting device 278 is illustrated in FIG. 18. Jetting device 278 preferably has a hollow cylindrical PZT core 296 which is intimately plated on the inside with a metallic conductor 298. It is intimately plated on the outside with a metallic conductor 300. The front of PZT tube 296 is closed by means of about a 0.002 thick disk of nickel alloy electroformed with a centralized about 50 micron opening and soldered to the end of the tube in contact with metallic conductor 298. The PZT tube may have an external diameter of about 0.075 inch O.D. with about a 0.05 inch I.D., which makes a very small device. Of course, the relative sizes may be scaled up preferably retaining a 50–60 micron opening 304. The interior 306 is a chamber which can be filled with a fluid through a connection 308 connecting a tube 310 leading to a fluid reservoir. It is also contemplated that the back end of PZT core tube 296 can be partially closed after filling the tube with a finite amount of volatile fluid to be ejected. That is, it can be a self-contained device.

Figure 19:
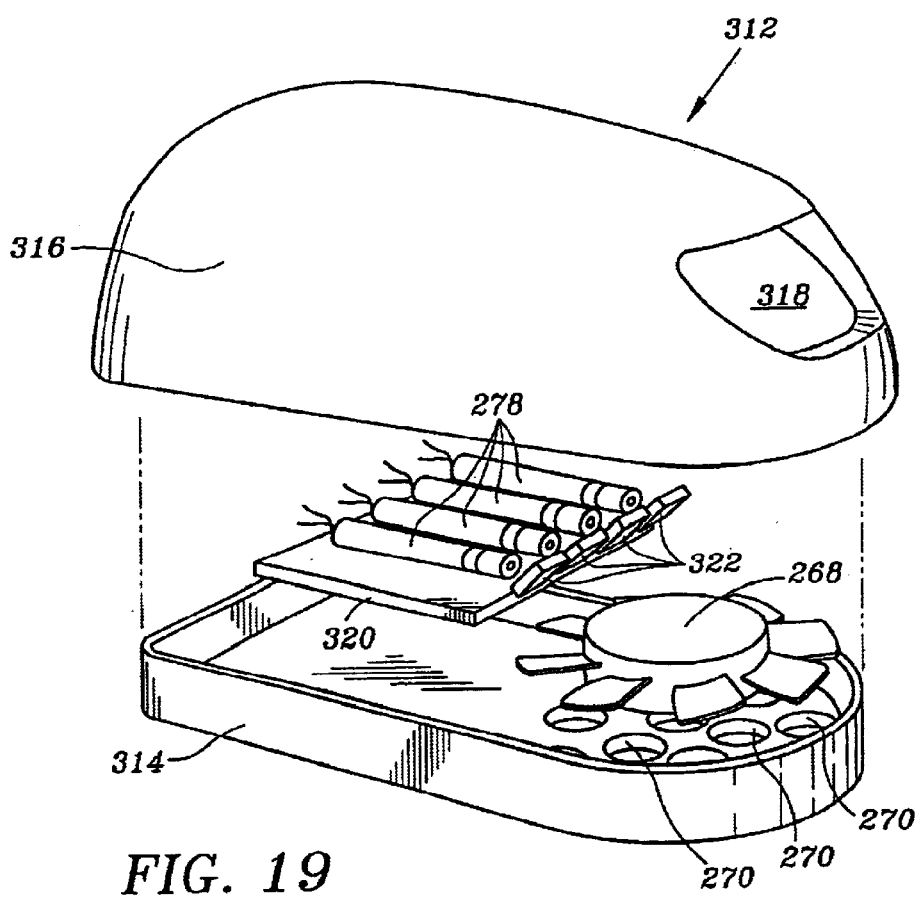
FIG. 19 is an alternate head for the fragrance dispensing stand of FIGS. 16 and 17 with the blower mounted in the head.

FIG. 19 is an alternate form of the dispensing stand illustrated in FIGS. 16 and 17 with an alternate head 312 which attaches to the upper end portion 272 of tube 266 or a smaller solid tube since no air passageway is required in this embodiment. Head 312 has a base 314 and a cover 316 having an opening in front 318. On a support plate 320 is mounted a plurality of ejection devices 278 each having an orifice aimed at a controllable heater 322. Of course, the number of these tiny ejection devices 278 and their corresponding accompanying heaters 322 could be greater in number than those shown. Air is drawn in through the openings 270 and the vaporized volatile material ejected from the jetting devices 278 or some combination of them passes through the outlet opening 318.

Other examples of the application of what may be referred to as "smell jets" which could dispense aromas, fragrances and vapors include computers with an attached or separate aroma box or headset; radio or television sets; automobiles, pagers or telephones; home appliances such as stand alone air fresheners, smoke detectors or artificial flowers; personal items such as eyeglasses, broaches or pocket units; and medical instruments or devices. A particular advantage of the fragrance ejection devices of the invention is the fact that they are easily battery powered and due to the advancement of wireless technology, can be operated by very small commercially available wireless communication devices which can receive wireless signals that could turn the ejection devices on and determine their operating rate, sequence of operations and operating frequency.

Figure 20:
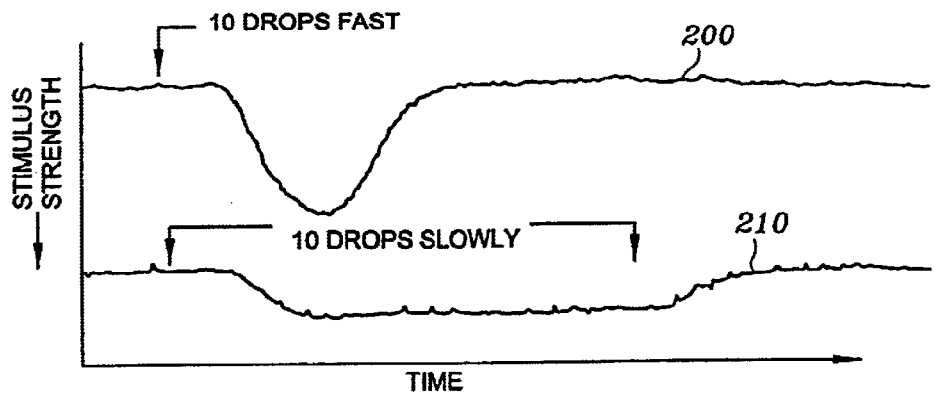
FIG. 20 depicts data showing a temporal response of different rates of dispensing fragrances.

FIG. 20 illustrates the sensory impact produced by the dispensing of ten drops fast in the upper graph 200 or ten drops slowly in the lower graph 210. (It should be noted that the vapor concentration increases toward the bottom of the page.) From the baseline, the vapor concentration increases very rapidly when the drops are distributed rapidly so the intensity is greater. In the lower graph, the intensity is less but the sensory experience is extended over a much longer period of time. This is one of the key advantages of this type of fragrance ejection device; the ability to vary the rate of change to impact the sensation produced by the fragrance.

Figure 21A:
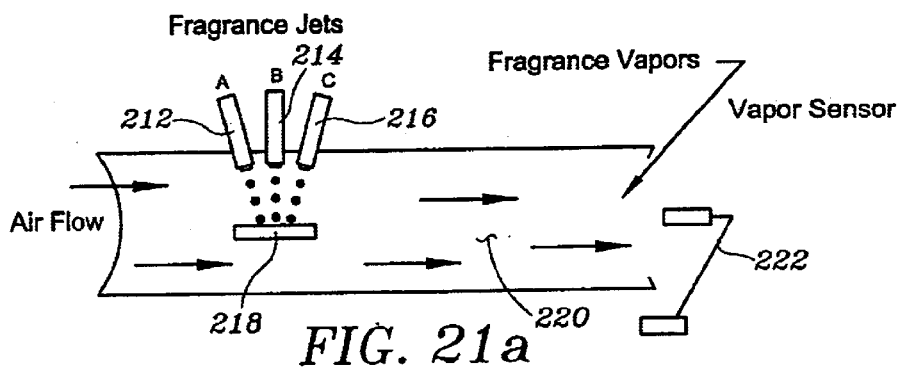
FIG. 21 illustrates the temporal response of a three-fluid dispensing system including a schematic of the system and an air-flow channel.
Figure 21B:
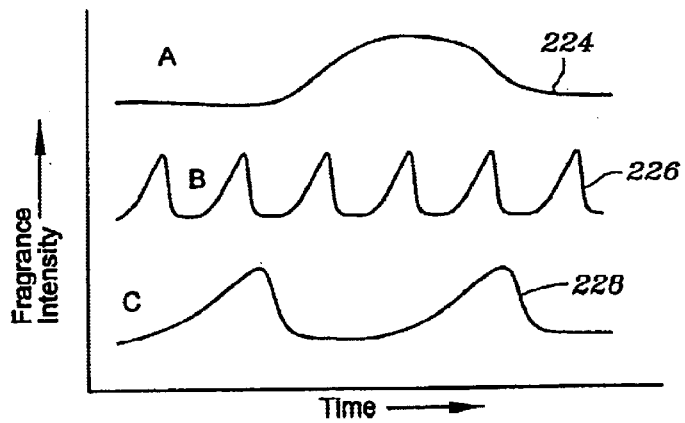

FIG. 21 schematically illustrates a similar type of experiment where ejection devices 212, 214 and 216 are denominated to produce fragrances A, B and C which are deposited upon a target surface 218 within an air flow passageway 220. Air flow is shown by the direction of the arrows. The fragrance intensity as illustrated as measured by a conventional electronic chemical sensor commonly referred to as an "electronic nose". This sensor produces a signal representative of the intensity. The fragrance intensity versus time is plotted below for each of the fragrances A, B and C. Curve 224 illustrates a slowly varying dispensing where the intensity of the fragrance A rises slowly and then after a time slowly declines. Curve 226 illustrates a rapid and regular change in the intensity level of the fragrance B. Curve 228 represents an intermediate level of fluctuation for fragrance C as compared to the curves for fragrances A and B. The varying results are produced in accordance with the quantum and rapidity of droplet ejection. One skilled in the art can understand that the number of fragrances could be expanded many times beyond that of three fragrances and the resulting fragrance could be produced as a combined fragrance by operating selected ones of the fragrance jets as indicated previously.

Figure 22:
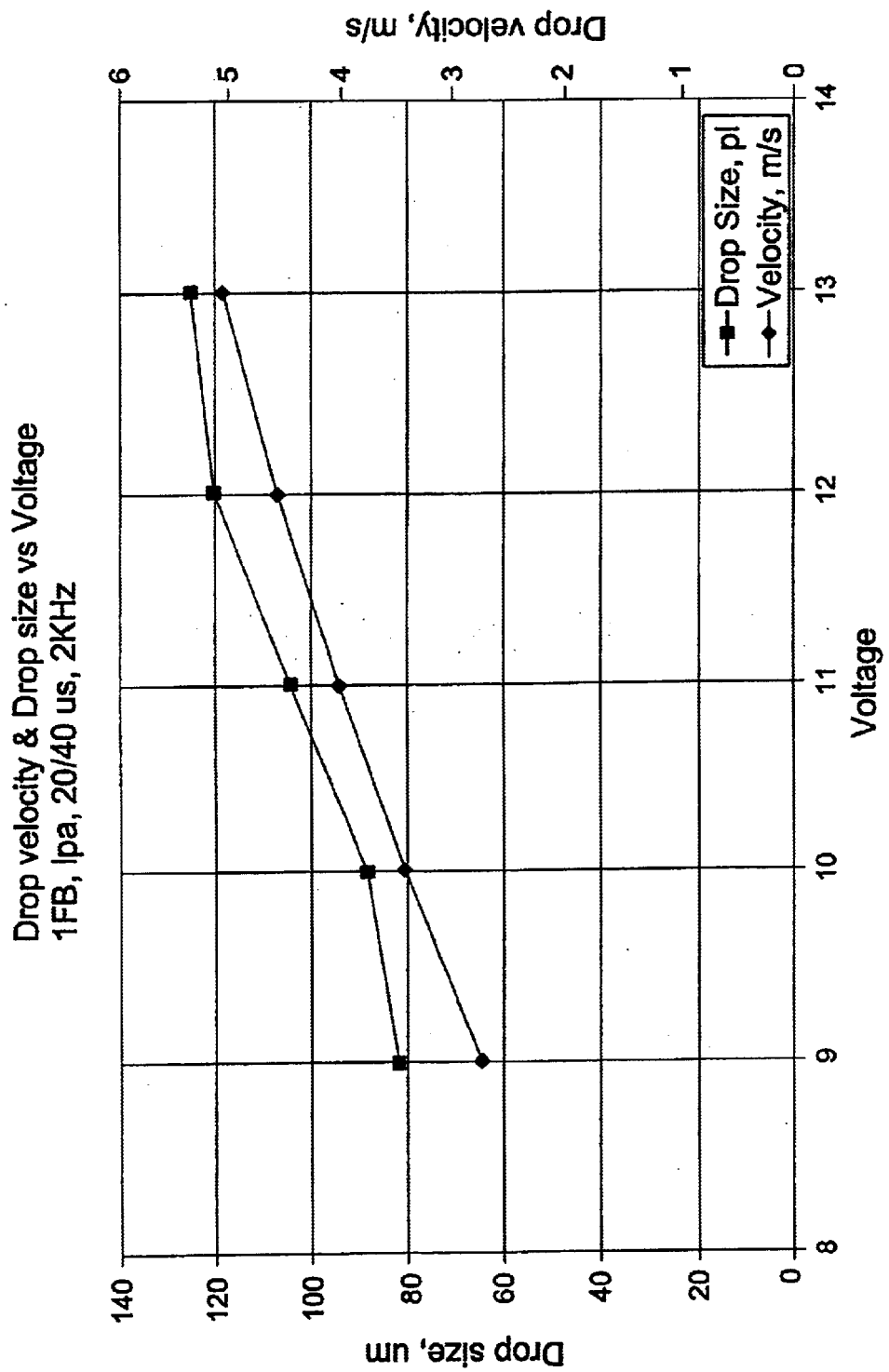
FIG. 22 presents droplet information data from one channel of a multi-fluid jetting device.

FIG. 22 is an actual graph of data taken from operation of the printhead like those shown in FIGS. 2, 3 and 4. A regular increase in drop size and velocity is observed jetting isopropyl alcohol at a droplet rate of 2000 droplets per second as the voltage is increased from eight to fourteen volts. Droplet size is shown in picoliters and velocity is measured in meters per second. A similar non-odor producing alcohol is commonly used as a solvent or diluent for fragrances although is it not the only solvent that may be used.

In an alternate embodiment, the invention can be used in combination with electronic chemical sensors which are increasing referred to in literature as "electronic noses". Electronic noses are discussed in some detail in the following references which are incorporated herein by reference. Baletz, Lange, and Koll, "The Electronic Nose in Lilliput", IEEE Spectrum, pp. 36–38, September 1998 and Kaplan and Braham, "The How and Why of Electronic Noses", IEEE Spectrum, pp. 22–34, September 1998. The former of these mentions an experimental electronic nose that could easily fit in a wristwatch. The invention provides a means for real time calibration of electronic chemical sensor arrays used in electronic noses which are capable of analyzing complex odors and vapors. Electronic noses work by comparing process signals from a sensor array with known patterns stored in a data base.

Various types of sensor arrays which are possible include conductive polymer sensors (U.S. Pat. Nos. 5,801,297; 5,145,645; 4,911,892; and 5,756,879), metal oxide conductivity sensors (U.S. Pat. No. 5,777,207), quartz resonator type sensors (U.S. Pat. No. 5,177,994), polymer dielectric sensors (capacitor), fluorescent optical sensors, etc. The type of sensor will determine the key features: number of sensor elements, detector sensitivity (threshold and response curve), stability, reproducability, response time and refresh time. The above mentioned U.S. patents are incorporated herein by reference.

The weaknesses of the present technology which this invention helps to overcome are the fact that electronic chemical sensors drift with time, temperature and relative humidity which affect the accuracy of their measurements. Refresh time tends to be long because a new baseline needs to be established prior to the next measurement; purging and back-fill with an external gas supply is costly and leads to a slow response system; and, if the relative humidity of the gas sample being measured is different from the calibration gas, then measurement errors will exist.

The invention is based upon the concept that a jetting device or ejecting device would dispense droplets of a calibration fluid onto a heated wick (target medium) in a passageway where a controlled airflow carries the calibration gas vapor over a sensor or array of sensors. Previous calibration of the ink-jet type ejection device establishes the number of calibration vapor molecules per cubic centimeter being delivered at the sensor site. By changing the number of drops, droplet size or the droplet rate, the molecular density could be increased or decreased. Naturally the calibration gas and vapor should be selected to be of the same character or even the same material itself which the sensor is intended to measure. In the sense that we are talking about an odor producing material being measured by the sensor, we are referring to volatile organic chemicals (VOC's) which are dispersed as vapor in the air or some environmental gas.

FIG. 23 is a schematic representation which illustrates the use of a microjet calibration system 324 which is located in a flow passage 326 which has additional inlets (ports) for odor producing volatile materials which are identified as VOCs 328 and purge gas 330. There is an inlet for a purge gas supply 330 with the gases all moving in the direction of the arrows in FIG. 23. Valves of some sort would be used to control the gas flow and to shut off any one of the inlets from items 324, 328, 330 so that the effect of one of them on the sensors 348 can be determined. System controller 356 opens and closes the inlet ports with valves (not shown).

FIG. 24 schematically represents ejection device 332 which is preferably a piezoelectric device such as described previously herein. Device 332 has an ejection orifice 334 and ejects droplets taken from a fluid reservoir 335 onto a preferably heated target medium 336 where the drops are volatilized to create a calibration gas. An air movement device such as a fan 338 in FIG. 23 and/or the opening 340 of the inlet into which the ejection device is directed are configured so that the concentration of calibration gas which is moving through housing 342 is carefully controlled and uniform. By evaporating a known volumetric amount of calibration fluid microdroplets 344 in a known flow of air or other environmental gas, an exact concentration of a calibration fluid can be repeatedly obtained. The beauty of the system is that it is nearly instantaneous since the droplet production can be started and stopped and operated at a precisely controlled rate by means of electronic signals controlled by a programmed system controller 356 together with drive electronics (not shown) as illustrated in the previous embodiments.

A sensor array 346 having a plurality of sensors 348 is positioned with respect to housing 342 to pass either calibration gas, purge gas or an unknown gas containing VOC's over the sensor array which may be referred to herein as "sensor". Raw signals from the sensor are transmitted to a digital signal processing unit 348 to identify the gas being exposed to the sensor. The signal processing unit is connected to a pattern recognition unit 350 which takes the processed signals from the signal processing unit and performs a number of operations. It is connected to database 352 containing key feature information for a large number of odors and vapors which are possible unknown VOCs. It sorts the data into key features and then compares the VOC features to information from either the microjet calibration system or the data base 352 of odors and vapors or both. System controller 356 controls a number of functions. It controls the gas handling system and fan 338 together with the microjet calibration system 324 and operates valves (not shown) which allow access to housing 342. It communicates with the signal processing unit and the pattern recognition unit which locates data from the database and communicates the information to the pattern recognition unit. It should be noted that with today's integrated circuit technology, one device could do the functions of several. For example, the signal processing unit, the pattern recognition unit, the memory for the data base and the system controller could all be built into one microprocessor-type unit.

The calibration signal produced by the sensor in response to a known concentration of calibration gas allows one to determine the sensor response to a like molecule and remove the background drift caused by relative humidity changes, temperature changes and use history. It is also useful to determine the threshold for sensors to specific molecules. For example, by increasing the known concentration of calibration gas in steps, it can be determined when a particular sensor reaches a detection threshold for that gas. The calibration fluid concentration preferably contains volatilized microdroplets from the same odor producing material to be sensed or a like-molecule. Because the individual microdroplets 344 are reproducible nearly exactly the same, we have the ability to predetermine the number of molecules per droplet in order to determine the concentration per unit volume. Although only one ejection device is schematically illustrated in FIGS. 23 and 24, it is understood that a plurality of ejection devices using printheads similar to FIGS. 2, 3, 4 and 5 can introduce a known concentration of multiple different calibration fluids to map additional sensors or accurately map the response of one sensor. The purge capability provided by purge gas unit 330 allows for determination of a baseline at a specific relative humidity. It also allows study of the optimum refresh cycle of the sensor array in cooperation with the microjet calibration system. After the response of the sensor array to introduction of VOC's 328 is performed, the VOC port can be closed by the system controller and the purge gas introduced to reverse the effect of the VOC's on the sensors in readiness for recalibration. The entry port to the purge gas is closed and the inlet port for the microjet calibration device is opened to operate device 334 to obtain a real time calibration. Then the calibration gas port is closed and the port from the VOC gas to be measured is opened whereby the baseline response of the sensors to the calibration gas may be used to adjust the value measured by the sensor from exposure to the unknown VOC's to produce a corrected result. A further indication of these characteristics are represented by reference to FIGS. 25–27.

An alternate location for sensor 346 denominated sensor 347 containing a single or a plurality of individual sensing elements 348 is shown in FIG. 24. In this arrangement the sensor is located in close proximity to where the calibration gas is being generated. This is more like a static arrangement where the calibration gas and sensor could be placed in an enclosure which could be purged with air or other gas periodically and samples of unknown gas introduced periodically. Still further, the sensor could be mounted on an arm that is periodically placed into the enclosure for calibration and/or purging to refresh it prior to being reexposed to an unknown sample gas.

Figure 25:
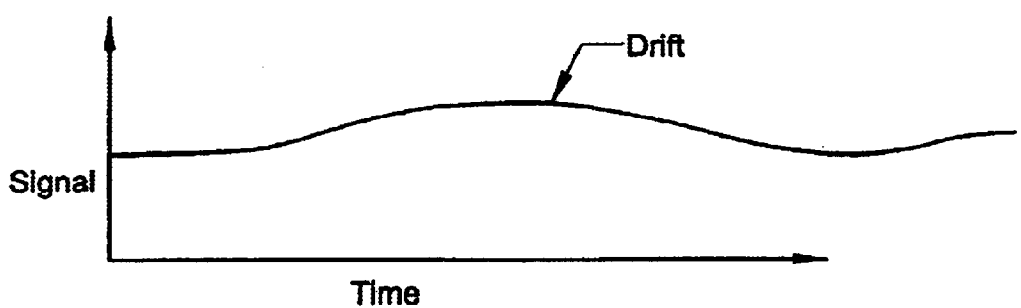
FIG. 25 illustrates the drift in signal of a sensor over time.

FIG. 25 indicates a signal produced by the sensor 346 plotted over time. The signal may drift as indicated because of the effect of factors mentioned previously.

Figure 26:
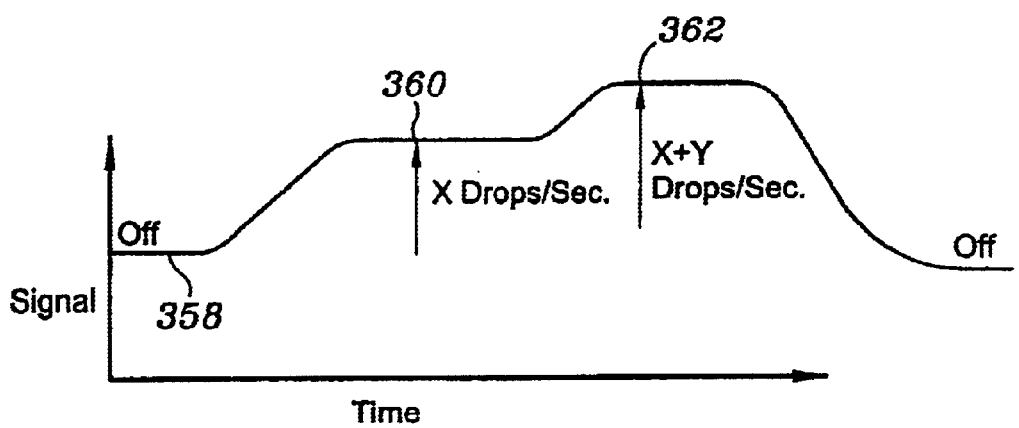
FIG. 26 illustrates the use of the microjet ejection system of FIG. 23 to present known concentrations of calibration gas to the sensor in real time.

FIG. 26 illustrates the signal from the sensors plotted over time with reference to the use of the microjet calibration system. The area 358 illustrates the off signal which may be indicative of the freshly purged sensor just before microjet calibration system 334 is turned on. Then calibration unit 334 is turned on at the rate of x drops per second to produce a response level 360 of the sensor 346 to a calibration gas of first concentration. This information will be stored by reference to the pattern recognition system and data base. Then calibration system 324 may be operated at an increased rate of x+y drops per second at 362 to generate a calibration gas of a second concentration which produces a response level 362. This information is likewise processed and stored. The information in FIG. 26 is used to establish the baseline response 360 and 362 of the electronic chemical sensor 346 to calibration gasses of first and second concentrations. Additional response points could be generated to produce a response curve of the sensor to specific known gas concentrations in real time. Then when the sensor is immediately thereafter exposed to a flow of air containing an unknown concentration of odor producing material, the response can be compared with the calibrated response to establish a value for the unknown concentration. Because of the proximity in time of the measurement to the calibration, the effects of drift are taken into account in making the concentration determination of the unknown. It is also possible to use an ejection device of device 334 to inject controlled amounts of water which are vaporized to produce known amounts of water vapor corresponding to relative humidity and thereby produce a real time relative humidity response curve for sensor 346. This can be combined with calibration gas results to generate a correction factor which can be applied later when sampling an unknown.

Figure 27:
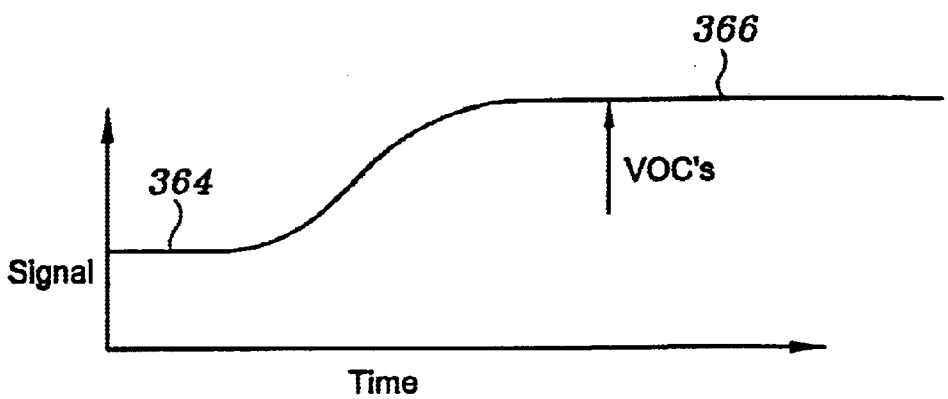
FIG. 27 illustrates the signal response of a sensor when exposed to a finite concentration of volatile organic chemicals.

Finally, FIG. 27 is indicative of the signal produced by sensor 346 from a pre-exposure baseline level 364 to a higher level 366 representative of exposure to air flow which contains the unknown VOC's. Immediately after this exposure, the port to the VOC's can be closed and the purge gas introduced for a short time followed by closing of the port to the purge gas and recalibration with the microjet unit 334 to confirm the value obtained in the test.

Those skilled in the art will appreciate that various modifications to the method and apparatus of the present invention may be made without departing from the scope of invention as defined in the appended claims.

What is claimed is:

1. A method to correct the measurement of an electronic chemical sensor used for measuring concentration of odors in air, comprising:

providing an electronic chemical sensor capable of generating a signal responsive to an amount of an odor producing material;

providing a support structure having a target medium, wherein the target medium comprises a heated target surface;

providing a printhead having at least one fluid ejection device having an orifice and being capable of ejecting microdroplets of calibration fluid at a controlled known rate;

ejecting a plurality of successive microdroplets of the calibration fluid on to the heated target surface thereby volatilizing the microdroplets to generate a calibration gas of a known first concentration;

exposing the electronic chemical sensor to the calibration gas of the first concentration;

establishing a baseline response of the electronic chemical sensor to the calibration gas of the first concentration;

exposing the electronic chemical sensor to air containing an unknown concentration of odor producing material and establishing a value for the unknown concentration; and adjusting the value for the unknown concentration by reference to the baseline response to the calibration gas to produce a corrected result.

2. The method of claim 1 and further including generating a calibration gas of known second concentration and exposing the calibration gas of the second concentration to the sensor and establishing the baseline response of the sensor to the calibration gas of the second concentration; wherein the value adjustment is made with reference to the baseline responses of the electronic chemical sensor to both of the baseline responses resulting from exposure of the sensor to the calibration gas of the first and second concentrations.

3. The method of claim 1 and further including purging the electronic chemical sensor with a flow of non-odor material containing gas prior to exposing the sensor to the flow of air containing an unknown concentration of odor producing material.

4. The method of claim 2 and further including purging the electronic chemical sensor with a flow of non-odor material containing gas prior to exposing the sensor to the flow of air containing an unknown concentration of odor producing material.

5. A calibration method for calibration of an electronic chemical sensor for measuring concentration of odors in air, comprising:

providing an electronic chemical sensor capable of generating a signal responsive to an amount of an odor producing material;

providing a support structure having a target medium, wherein the target medium comprises a heated target surface;

providing a printhead having at least one fluid ejection device having an orifice and being capable of ejecting microdroplets of calibration fluid at a controlled known rate;

ejecting a plurality of successive microdroplets of the calibration fluid on to the heated target surface thereby volatilizing the microdroplets to generate a calibration gas of a known first concentration; and exposing the electronic chemical sensor to the calibration gas of the known first concentration to obtain a sensor calibration signal representative of the known first concentration.

6. A method to correct the measurement of an electronic chemical sensor used for measuring concentration of odors in air comprising;

providing a plurality of electronic chemical sensors capable of generating a signal response to an amount of an odor producing material vapor, including at least a first sensor and a second sensor responsive respectively to a first and a second odor producing material vapor;

providing a support structure having a target medium, wherein the target medium comprises a first and a second heated surface;

providing a printhead having a plurality of fluid ejection devices each having an orifice and fluid reservoir and being capable of ejecting microdroplets of calibration fluid at a controlled known rate, including at least a first ejection device having a first reservoir and a second ejection device having a second reservoir wherein the first and second reservoirs, respectively, contain a first and a second calibration fluid;

ejecting a plurality of successive microdroplets of the first calibration fluid from the first ejection device on to the first heated target surface and ejecting a plurality of successive microdroplets of the second calibration fluid from the second ejection device on to the second heated target surface thereby volatilizing the microdroplets to generate a first mixed calibration gas of the known first and second calibration fluid vapor concentrations;

exposing the plurality of electronic sensors to the mixed calibration gas;

establishing a baseline response of the at least first and second electronic chemical sensors to the mixed calibration gas of the first and second calibration vapor concentrations;

exposing the plurality of electronic sensors to air containing an unknown mixed concentration of components of odor producing material and establishing a value for at least one component of the unknown mixed concentration of odor producing material; and adjusting the value for the at least one component of the unknown mixed concentration by reference to the baseline response to the calibration gas to produce a corrected result.

7. The method of claim 6 and further including generating a second mixed calibration gas of a known second concentration and exposing the second mixed calibration gas of the second concentration to the plurality of sensors and establishing the baseline response of the sensors to the second mixed calibration gas of the second concentration; wherein the value adjustment is made with reference to the baseline responses of the electronic chemical sensor to both of the baseline responses resulting from exposure of the sensors to both the first and second mixed calibration gas.

8. The method of claim 7 and further including purging the electronic chemical sensor with a flow of non-odor material containing gas prior to exposing the sensor to air containing an unknown concentration of odor producing material.

* * * * *